United States Patent
Schulhauser et al.

(10) Patent No.: US 12,263,020 B2
(45) Date of Patent: Apr. 1, 2025

(54) SYSTEMS AND METHODS FOR DETECTING STROKES

(71) Applicant: Covidien LP, Mansfield, MA (US)

(72) Inventors: Randal C. Schulhauser, Phoenix, AZ (US); John Wainwright, Foothill Ranch, CA (US); Eric J. Panken, Edina, MN (US); Jadin C. Jackson, Roseville, MN (US); Alejo Chavez Gaxiola, Tempe, AZ (US); Aaron Gilletti, Costa Mesa, CA (US); Eduardo N. Warman, Maple Grove, MN (US); Paul G. Krause, Shoreview, MN (US); Eric M. Christensen, Gilbert, AZ (US); Patrick W. Kinzie, Glendale, AZ (US); Julia Slopsema, Fridley, MN (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 17/006,444

(22) Filed: Aug. 28, 2020

(65) Prior Publication Data
US 2021/0251578 A1 Aug. 19, 2021

Related U.S. Application Data

(60) Provisional application No. 62/977,503, filed on Feb. 17, 2020.

(51) Int. Cl.
*A61B 5/00* (2006.01)
*A61B 5/0205* (2006.01)
(Continued)

(52) U.S. Cl.
CPC .......... *A61B 5/7282* (2013.01); *A61B 5/0205* (2013.01); *A61B 5/1117* (2013.01);
(Continued)

(58) Field of Classification Search
None
See application file for complete search history.

(56) References Cited

U.S. PATENT DOCUMENTS

| 4,201,222 A | 5/1980 | Haase |
| 4,907,597 A | 3/1990 | Chamoun |

(Continued)

FOREIGN PATENT DOCUMENTS

| AU | 2014228116 B2 | 1/2019 |
| CN | 1891144 A | 1/2007 |

(Continued)

OTHER PUBLICATIONS

Routray et al., "ECG Artifact Removal of EEG signal using Adaptive Neural Network," 2018 IEEE 13th International Conference on Industrial and Information Systems (ICIIS), May 27, 2019, 4 pages.

(Continued)

*Primary Examiner* — Joseph M Dietrich
(74) *Attorney, Agent, or Firm* — Shumaker & Sieffert, P.A.

(57) ABSTRACT

A system for detecting strokes includes a sensor device configured to obtain physiological data from a patient, for example brain activity data. The sensor device can include electrodes configured to be disposed at the back of the patient's neck or base of the skull. The electrodes can detect electrical signals corresponding to brain activity in the P3, Pz, and/or P4 brain regions or other brain regions. A computing device communicatively coupled to the sensor device is configured to receive the physiological data and analyze it to indicate whether the patient has suffered a stroke.

35 Claims, 11 Drawing Sheets

(51) Int. Cl.
   *A61B 5/11*    (2006.01)
   *A61B 5/283*   (2021.01)
   *A61B 5/291*   (2021.01)
   *A61B 5/316*   (2021.01)

(52) U.S. Cl.
   CPC .............. *A61B 5/283* (2021.01); *A61B 5/291* (2021.01); *A61B 5/316* (2021.01); *A61B 5/486* (2013.01); *A61B 5/6822* (2013.01); *A61B 5/6861* (2013.01); *A61B 5/7203* (2013.01); *A61B 5/7264* (2013.01); *A61B 5/7275* (2013.01); *A61B 5/747* (2013.01)

(56) References Cited

U.S. PATENT DOCUMENTS

| | | |
|---|---|---|
| 5,029,590 A | 7/1991 | Allain et al. |
| 5,305,746 A | 4/1994 | Fendrock |
| 5,458,117 A | 10/1995 | Chamoun et al. |
| 6,032,064 A | 2/2000 | Devlin et al. |
| 6,728,564 B2 | 4/2004 | Laehteenmaeki |
| 6,961,601 B2 | 11/2005 | Matthews et al. |
| 7,054,453 B2 | 5/2006 | Causevic et al. |
| 7,054,454 B2 | 5/2006 | Causevic et al. |
| 7,072,705 B2 | 7/2006 | Miga et al. |
| 7,130,673 B2 | 10/2006 | Tolvanen-Laakso et al. |
| 7,367,949 B2 | 5/2008 | Korhonen et al. |
| 7,398,115 B2 | 7/2008 | Lynn |
| 7,407,485 B2 | 8/2008 | Huiku |
| 7,447,541 B2 | 11/2008 | Huiku et al. |
| 7,471,978 B2 | 12/2008 | John et al. |
| 7,904,144 B2 | 3/2011 | Causevic et al. |
| 8,323,188 B2 | 12/2012 | Tran |
| 8,364,254 B2 | 1/2013 | Jacquin et al. |
| 8,370,287 B2 | 2/2013 | Snyder |
| 8,423,145 B2 | 4/2013 | Pless et al. |
| 8,603,014 B2 | 12/2013 | Alleman et al. |
| 8,837,800 B1 | 9/2014 | Bammer et al. |
| 8,862,199 B2 | 10/2014 | Ko et al. |
| 8,926,509 B2 | 1/2015 | Magar et al. |
| 9,119,656 B2 | 9/2015 | Bose et al. |
| 9,126,018 B1 | 9/2015 | Garrison |
| 9,149,229 B1 | 10/2015 | Tarler |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,370,313 B2 | 6/2016 | Mcpeck et al. |
| 9,399,118 B2 | 7/2016 | Kume et al. |
| 9,408,575 B2 | 8/2016 | Bordoley et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,532,748 B2 | 1/2017 | Denison et al. |
| 9,539,022 B2 | 1/2017 | Bowman |
| 9,561,345 B2 | 2/2017 | Garrison et al. |
| 9,579,028 B2 | 2/2017 | Bonmassar et al. |
| 9,579,119 B2 | 2/2017 | Cully et al. |
| 9,585,741 B2 | 3/2017 | Ma |
| D784,542 S | 4/2017 | Zwierstra et al. |
| 9,642,635 B2 | 5/2017 | Vale et al. |
| 9,655,633 B2 | 5/2017 | Leynov et al. |
| 9,675,264 B2 | 6/2017 | Acquista et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,878,160 B2 | 1/2018 | Pless et al. |
| 9,943,690 B2 | 4/2018 | Pless et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,182,723 B2 | 1/2019 | Evans et al. |
| 10,195,402 B2 | 2/2019 | Zhadkevich |
| 10,252,058 B1 | 4/2019 | Fuerst |
| 10,281,478 B2 | 5/2019 | Franco |
| 10,285,606 B2 | 5/2019 | Jensen |
| 10,285,617 B2 | 5/2019 | Toth et al. |
| 10,335,083 B2 | 7/2019 | Keteyian et al. |
| 10,398,319 B2 | 9/2019 | Wang et al. |
| 10,463,271 B2 | 11/2019 | Intrator |
| 10,555,861 B2 | 2/2020 | Zwierstra et al. |
| 10,575,741 B2 | 3/2020 | Kim et al. |
| 10,575,818 B2 | 3/2020 | O'Brien et al. |
| 10,610,200 B2 | 4/2020 | Arant et al. |
| 10,616,473 B2 | 4/2020 | Costa et al. |
| 10,617,388 B2 | 4/2020 | Flores, II et al. |
| 10,743,809 B1 | 8/2020 | Kamousi et al. |
| 10,779,747 B2 | 9/2020 | Simon |
| 10,786,209 B2 | 9/2020 | Park et al. |
| 11,006,841 B2 | 5/2021 | Wainwright et al. |
| 11,399,761 B2 | 8/2022 | Intrator |
| 11,457,866 B2 | 10/2022 | Kesinger et al. |
| 2002/0002390 A1 | 1/2002 | Fischell et al. |
| 2002/0099412 A1 | 7/2002 | Fischell et al. |
| 2002/0169485 A1 | 11/2002 | Pless et al. |
| 2003/0093004 A1 | 5/2003 | Sosa et al. |
| 2004/0077967 A1* | 4/2004 | Jordan ................... A61B 5/316 600/544 |
| 2004/0163648 A1 | 8/2004 | Burton |
| 2004/0220644 A1 | 11/2004 | Shalev et al. |
| 2004/0243017 A1 | 12/2004 | Causevic |
| 2004/0267153 A1 | 12/2004 | Bergethon |
| 2005/0113704 A1 | 5/2005 | Lawson et al. |
| 2005/0203366 A1 | 9/2005 | Donoghue et al. |
| 2006/0217614 A1 | 9/2006 | Takala et al. |
| 2006/0224421 A1 | 10/2006 | St. Ores et al. |
| 2007/0010723 A1 | 1/2007 | Uutela et al. |
| 2007/0021687 A1 | 1/2007 | Keith et al. |
| 2007/0032736 A1 | 2/2007 | Finnigan et al. |
| 2007/0167694 A1 | 7/2007 | Causevic et al. |
| 2007/0239054 A1 | 10/2007 | Giftakis et al. |
| 2007/0249954 A1 | 10/2007 | Virag et al. |
| 2007/0276270 A1 | 11/2007 | Tran |
| 2008/0081980 A1 | 4/2008 | Maschke et al. |
| 2008/0139908 A1 | 6/2008 | Kurth |
| 2008/0167540 A1 | 7/2008 | Korhonen et al. |
| 2008/0208073 A1 | 8/2008 | Causevic |
| 2008/0208074 A1 | 8/2008 | Snyder et al. |
| 2008/0243021 A1 | 10/2008 | Causevic et al. |
| 2008/0294019 A1 | 11/2008 | Tran |
| 2009/0099624 A1* | 4/2009 | Kokones ............... A61B 5/6885 607/59 |
| 2009/0247894 A1 | 10/2009 | Causevic |
| 2009/0290772 A1 | 11/2009 | Avinash et al. |
| 2010/0217147 A1 | 8/2010 | Odame |
| 2010/0274152 A1 | 10/2010 | Mcpeck et al. |
| 2011/0053859 A1 | 3/2011 | Deadwyler et al. |
| 2011/0066055 A1 | 3/2011 | Bharmi et al. |
| 2011/0245633 A1 | 10/2011 | Goldberg et al. |
| 2011/0245707 A1 | 10/2011 | Castle et al. |
| 2011/0301448 A1 | 12/2011 | deCharms |
| 2013/0009783 A1 | 1/2013 | Tran |
| 2013/0030461 A1 | 1/2013 | Marks et al. |
| 2013/0231947 A1 | 9/2013 | Shusterman |
| 2013/0281788 A1 | 10/2013 | Garrison |
| 2013/0303900 A1 | 11/2013 | Nowinski |
| 2014/0187973 A1 | 7/2014 | Brown et al. |
| 2014/0276074 A1 | 9/2014 | Warner |
| 2014/0276123 A1 | 9/2014 | Yang |
| 2014/0316230 A1 | 10/2014 | Denison et al. |
| 2014/0343595 A1 | 11/2014 | Monstadt et al. |
| 2015/0157235 A1 | 6/2015 | Jelen et al. |
| 2015/0157273 A1 | 6/2015 | An et al. |
| 2015/0359547 A1 | 12/2015 | Vale et al. |
| 2015/0366518 A1* | 12/2015 | Sampson ............... A61B 5/7275 600/509 |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |

(56) References Cited

U.S. PATENT DOCUMENTS

| | | |
|---|---|---|
| 2016/0128592 A1 | 5/2016 | Rosen et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0256130 A1 | 9/2016 | Hamilton et al. |
| 2016/0278736 A1 | 9/2016 | Hamilton et al. |
| 2016/0296690 A1 | 10/2016 | Kume et al. |
| 2016/0302808 A1 | 10/2016 | Loganathan et al. |
| 2016/0331255 A1 | 11/2016 | Cheatham, III et al. |
| 2016/0367217 A1 | 12/2016 | Flores, II et al. |
| 2016/0375180 A1 | 12/2016 | Anzai |
| 2017/0007167 A1 | 1/2017 | Kostic et al. |
| 2017/0020454 A1 | 1/2017 | Keteyian et al. |
| 2017/0055839 A1 | 3/2017 | Levinson et al. |
| 2017/0071495 A1 | 3/2017 | Denison et al. |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0119347 A1 | 5/2017 | Flores, II et al. |
| 2017/0127946 A1 | 5/2017 | Levinson et al. |
| 2017/0164963 A1 | 6/2017 | Goyal |
| 2017/0188993 A1 | 7/2017 | Hamilton et al. |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0307420 A1 | 10/2017 | Flores, II et al. |
| 2017/0319099 A1 | 11/2017 | Levinson et al. |
| 2018/0021021 A1 | 1/2018 | Zwierstra et al. |
| 2018/0049762 A1 | 2/2018 | Seip et al. |
| 2018/0064364 A1 | 3/2018 | Oziel et al. |
| 2018/0084982 A1 | 3/2018 | Yamashita et al. |
| 2018/0103927 A1 | 4/2018 | Chung et al. |
| 2018/0116717 A1 | 5/2018 | Taff et al. |
| 2018/0117331 A1 | 5/2018 | Kuzniecky et al. |
| 2018/0132876 A1 | 5/2018 | Zaidat |
| 2018/0140203 A1 | 5/2018 | Wang et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0153477 A1 | 6/2018 | Nagale |
| 2018/0185614 A1 | 7/2018 | Garrison et al. |
| 2018/0220919 A1 | 8/2018 | Wershing et al. |
| 2018/0220991 A1 | 8/2018 | O'Brien et al. |
| 2018/0249967 A1 | 9/2018 | Lederman et al. |
| 2018/0353084 A1 | 12/2018 | Wainright et al. |
| 2019/0021627 A1 | 1/2019 | Levinson et al. |
| 2019/0021665 A1 | 1/2019 | Kesinger et al. |
| 2019/0051409 A1 | 2/2019 | Petrossian et al. |
| 2019/0059850 A1 | 2/2019 | Zwierstra et al. |
| 2019/0099132 A1 | 4/2019 | Mulinti et al. |
| 2019/0175433 A1 | 6/2019 | Zwierstra et al. |
| 2019/0200954 A1 | 7/2019 | Flores, II et al. |
| 2019/0209128 A1 | 7/2019 | O'Brien et al. |
| 2019/0209141 A1 | 7/2019 | O'Brien et al. |
| 2019/0216433 A1 | 7/2019 | Hamilton et al. |
| 2019/0223830 A1 | 7/2019 | Thorpe et al. |
| 2019/0223837 A1 | 7/2019 | Petrossian et al. |
| 2019/0282318 A1 | 9/2019 | Arant et al. |
| 2019/0298210 A1 | 10/2019 | Bennet et al. |
| 2019/0357845 A1 | 11/2019 | Willis et al. |
| 2019/0365274 A1 | 12/2019 | Wyeth et al. |
| 2020/0000355 A1 | 1/2020 | Khair |
| 2020/0008697 A1 | 1/2020 | Kesinger et al. |
| 2020/0085255 A1 | 3/2020 | Yoo et al. |
| 2020/0085525 A1 | 3/2020 | Zwierstra et al. |
| 2020/0100974 A1 | 4/2020 | Hewes et al. |
| 2021/0030299 A1 | 2/2021 | Naber et al. |
| 2021/0241908 A1 | 8/2021 | Ciupa et al. |
| 2021/0251497 A1 | 8/2021 | Schulhauser et al. |
| 2021/0259621 A1 | 8/2021 | Alves et al. |
| 2021/0267465 A1 | 9/2021 | Wainwright et al. |
| 2021/0378582 A1 | 12/2021 | Day et al. |
| 2022/0022800 A1 | 1/2022 | Abrams et al. |
| 2022/0061678 A1 | 3/2022 | Schulhauser et al. |
| 2022/0061742 A1 | 3/2022 | Panken et al. |
| 2022/0071547 A1 | 3/2022 | Revels et al. |
| 2022/0183633 A1 | 6/2022 | Kinzie et al. |
| 2022/0203091 A1 | 6/2022 | Vysokov |
| 2022/0296174 A1 | 9/2022 | Kinzie et al. |

FOREIGN PATENT DOCUMENTS

| | | |
|---|---|---|
| CN | 1891145 A | 1/2007 |
| CN | 105792741 A | 7/2016 |
| CN | 108834398 A | 11/2018 |
| CN | 110612057 A | 12/2019 |
| DE | 102014100133 B4 | 8/2016 |
| EP | 2319575 A1 | 5/2011 |
| EP | 3068294 A1 | 9/2016 |
| JP | 2014004219 A | 1/2014 |
| JP | 2018118132 A | 8/2018 |
| JP | 2020511173 A | 4/2020 |
| KR | 20180102877 A | 9/2018 |
| WO | 2013110001 A1 | 7/2013 |
| WO | 2013165474 A1 | 11/2013 |
| WO | 2015073903 A1 | 5/2015 |
| WO | 2015141317 A1 | 9/2015 |
| WO | 2016036461 A1 | 3/2016 |
| WO | 2017049628 A1 | 3/2017 |
| WO | 2017120382 A1 | 7/2017 |
| WO | 2017189623 A1 | 11/2017 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018089035 A1 | 5/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018184776 A1 | 10/2018 |
| WO | 2018201190 A1 | 11/2018 |
| WO | 2019004710 A1 | 1/2019 |
| WO | 2019094877 A1 | 5/2019 |
| WO | 2019166557 A1 | 9/2019 |
| WO | 2019177630 A1 | 9/2019 |
| WO | 2019190583 A1 | 10/2019 |
| WO | 2019195844 A1 | 10/2019 |
| WO | 2019199334 A1 | 10/2019 |
| WO | 2020144687 A1 | 7/2020 |
| WO | 2021167988 A1 | 8/2021 |
| WO | 2021181395 A1 | 9/2021 |
| WO | 2022011077 A1 | 1/2022 |
| WO | 2022020339 A1 | 1/2022 |
| WO | 2022047066 A1 | 3/2022 |
| WO | 2022047215 A1 | 3/2022 |
| WO | 2022055948 A1 | 3/2022 |
| WO | 2022132938 A1 | 6/2022 |
| WO | 2022170150 A1 | 8/2022 |

OTHER PUBLICATIONS

Ponciano et al., "Experimental Study for Determining the Parameters Required for Detecting ECG and EEG Related Diseases During the Timed-Up and Go Test," Aug. 27, 2020, 21 pages.

Giri et al., "Ischemic Stroke Identification Based on EEG and EOG using 1D Convolutional Neural Network and Batch Normalization," ICACSIS 2016, IEEE, Oct. 15, 2016, 8 pp.

International Search Report and Written Opinion of International Application No. PCT/US2021/018394, dated Jun. 1, 2021, 15 pp.

Response to Office Action dated Sep. 9, 2022 from U.S. Appl. No. 17/176,504, filed Dec. 9, 2022, 11 pp.

Office Action from U.S. Appl. No. 17/176,504 dated Sep. 9, 2022, 15 pp.

Final Office Action from U.S. Appl. No. 17/176,504 dated Apr. 4, 2023, 9 pp.

Response to Final Office Action dated Apr. 4, 2023 from U.S. Appl. No. 17/176,504, filed May 26, 2023, 5 pp.

(56) References Cited

OTHER PUBLICATIONS

Notice of Allowance from U.S. Appl. No. 17/176,504 dated Jun. 22, 2023, 8 pp.
Hu et al., "Intelligent Sensor Networks—The Integration of Sensor Networks, Signal Processing and Machine Learning", CRC Press, Boca Raton, Mar. 20, 2013, 674 pp., https://doi.org/10.1201/b14300.
Huang et al., "Kernal Based Algorthims for Mining Huge Data Sets—Supervised, Semi-Supervised, and Unsupervised Learning", Studies in Computational Intelligence, vol. 17, Springer, The Netherlands, Jan. 2006, 266 pp., doi:10.1007/3-540-31689-2.
Notice of Allowance from U.S. Appl. No. 17/176,504 dated Sep. 29, 2023, 8 pp.
Communication pursuant to Article 94(3) EPC from counterpart European Application No. 21711121.0 dated Nov. 3, 2001, 5 pp.
Office Action from U.S. Appl. No. 17/176,504 dated Feb. 1, 2024, 13 pp.
Response to Office Action dated Feb. 1, 2024 from U.S. Appl. No. 17/176,504, filed Apr. 17, 2024, 11 pp.
Final Office Action from U.S. Appl. No. 17/176,504 dated Sep. 11, 2024, 16 pp.
First Office Action and Search Report, and translation thereof, from counterpart Chinese Application No. 202180014972.4 dated Jul. 31, 2024, 15 pp.
Notice of Allowance from U.S. Appl. No. 17/176,504 dated Dec. 4, 2024, 7 pp.
Response to Final Office Action dated Sep. 11, 2024 from U.S. Appl. No. 17/176,504, filed Nov. 11, 2024, 12 pp.

\* cited by examiner

SYSTEMS AND METHODS FOR DETECTING STROKES

This application claims the benefit of U.S. Provisional Application No. 62/997,503, filed Feb. 17, 2020, the entire content of which is incorporated herein by reference.

FIELD

The present technology is directed to medical devices and, more particularly, to systems and methods for detecting strokes.

BACKGROUND

Stroke is a serious medical condition that can cause permanent neurological damage, complications, and death. Stroke may be characterized as the rapidly developing loss of brain functions due to a disturbance in the blood vessels supplying blood to the brain. The loss of brain functions can be a result of ischemia (lack of blood supply) caused by thrombosis or embolism. During a stroke, the blood supply to an area of a brain may be decreased, which can lead to dysfunction of the brain tissue in that area.

Stroke is the number two cause of death worldwide and the number one cause of disability. Speed to treatment is the critical factor in stroke treatment as 1.9 M neurons are lost per minute on average during stroke. Stroke diagnosis and time between event and therapy delivery are the primary barriers to improving therapy effectiveness. Stroke has 3 primary etiologies; i) ischemic stroke (representing about 65% of all strokes), ii) hemorrhagic stroke (representing about 10% of all strokes), and iii) cryptogenic strokes (includes TIA, representing 25% of all strokes). Strokes can be considered as having neurogenic and/or cardiogenic origins.

A variety of approaches exist for treating patients undergoing a stroke. For example, a clinician may administer anticoagulants, such as warfarin, or may undertake intravascular interventions such as thrombectomy procedures to treat ischemic stroke. For example, a clinician may administer antihypertensive drugs, such as beta blockers (e.g., Labetalol) and ACE-inhibitors (e.g., Enalapril) or may undertake intravascular interventions such as coil embolization to treat hemorrhagic stroke. Lastly, if stroke symptoms have resolved on their own with negative neurological work-up, a clinician may administer long-term cardiac monitoring (external or implantable) to determine potential cardiac origins of cryptogenic stroke. However, such treatments may be frequently underutilized and/or relatively ineffective due to the failure to timely identify whether a patient is undergoing or has recently undergone a stroke. This is a particular risk with more minor strokes that leave patients relatively functional upon cursory evaluation.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A stroke detection system, comprising:
   a sensor device configured to obtain physiological data from a patient; and
   a computing device communicatively coupled to the sensor device, the computing device configured to:
   receive the physiological data from the sensor device;
   analyze the physiological data; and
   based on the analysis, provide a patient stroke indicator.
2. The system of Clause 1, wherein the physiological data comprises brain activity data.
3. The system of any one of the Clauses herein, wherein the sensor device comprises a plurality of electrodes configured to detect brain activity data corresponding to activity in at least one of the P3, Pz, and P4 brain regions.
4. The system of any one of the Clauses herein, wherein the sensor device comprises a plurality of electrodes configured to detect brain activity data corresponding to activity in each of the P3, Pz, and P4 brain regions.
5. The system of any one of the Clauses herein, wherein the sensor device is configured to be disposed at or adjacent a rear portion of the patient's neck or skull base.
6. The system of any one of the Clauses herein, wherein the sensor device is configured to be disposed above the patient's shoulders.
7. The system of any one of the Clauses herein, wherein the sensor device is configured to be disposed at or below the patient's occipital bone.
8. The system of any one of the Clauses herein, wherein the sensor device comprises a housing configured to be implanted within the patient.
9. The system of Clause 9, wherein the housing is configured to be implanted subcutaneously.
10. The system of any one of the Clauses herein, wherein sensor device comprises a housing configured to be disposed over the patient's skin.
11. The system of Clause 10, wherein the sensor device includes electrodes configured to contact the patient's skin.
12. The system of Clause 11, wherein the electrodes include protrusions configured to at least partially penetrate the patient's skin.
13. The system of Clause 12, wherein the protrusions comprise microneedles.
14. The system of any one of the Clauses herein, wherein the sensor device comprises an EEG array.
15. The method of Clause 14, wherein the EEG array comprises at least 2, at least 3, at least 4, or at least 5 electrodes.
16. The method of Clause 14, wherein the EEG array comprises fewer than 6, fewer than 5, fewer than 4, or fewer than 3 electrodes.
17. The system of any one of the Clauses herein, wherein the sensor device comprises a housing having a volume of less than about 1.5 cc, about 1.4 cc, about 1.3 cc, about 1.2 cc, about 1.1 cc, about 1.0 cc, about 0.9 cc, about 0.8 cc, about 0.7 cc, about 0.6 cc, about 0.5 cc, or about 0.4 cc.
18. The system of any one of the Clauses herein, wherein the sensor device comprises a housing having a lower surface configured to face towards the patient's tissue, an upper surface opposite the lower surface, and a thickness extending between the lower surface and the upper surface.
19. The system of Clause 18, wherein the housing comprises multiple sub-housings coupled together by flexible members or conductors.

20. The system of Clause 19, wherein electrodes of the sensor device are distributed among the sub-housings.
21. The system of Clause 18, wherein the housing is flexible such that lateral end portions can move anteriorly relative to a central portion of the housing.
22. The system of Clause 21, wherein one electrode is disposed at each of the lateral end portions.
23. The system of Clause 21 or 22, wherein at least one electrode is disposed in the central portion of the housing.
24. The system of any one of Clauses 18-23, wherein the thickness is less than about 10 mm, about 9 mm, about 8 mm, about 7 mm, about 6 mm, about 5 mm, about 4 mm, or about 3 mm.
25. The system of any one of Clauses 18-24, wherein the electrodes of the sensor device are exposed along the lower surface.
26. The system of Clause 25, wherein the sensor device comprises at least three electrodes exposed along the lower surface, and wherein the three electrodes are not aligned along a common axis.
27. The system of Clause 26, wherein housing is elongated along a horizontal axis, and wherein a first electrode is disposed substantially centrally along the horizontal axis, a second electrode is spaced apart from the first electrode along the horizontal axis in a first direction, and wherein the third electrode is spaced apart from the first electrode along the horizontal axis in a second direction opposite the first.
28. The system of Clause 26, wherein the housing is elongated along a first horizontal axis, and wherein a first electrode is disposed substantially centrally along the horizontal axis, a second electrode is disposed towards a first end portion of the housing along the horizontal axis.
29. The system of any one of Clauses 17-28, wherein the upper and lower surface form a substantially boomerang or chevron shape.
30. The system of any one of the Clauses herein, wherein one or more electrodes are disposed on a first major surface of the device and one or more electrodes are disposed on a second, opposite major surface of the device.
31. The system of any one of the Clauses herein, wherein the sensor device comprises a housing configured to be delivered through a trocar introducer.
32. The system of any one of the Clauses herein, wherein the sensor device and the computing device are enclosed within a common housing.
33. The system of any one of the Clauses herein, wherein the physiological data comprises at least three channels of EEG signals.
34. The system of any one of the Clauses herein, wherein the physiological data comprises electrical brain activity data and electrical heart activity data, and wherein analyzing the physiological data comprises filtering the physiological data to separate the electrical brain activity data from the electrical heart activity data.
35. The system of any one of the Clauses herein, wherein the physiological data comprises electrical signals detected via electrodes of the sensor device, and wherein analyzing the physiological data comprises analyzing the electrical signals to detect brain activity.
36. The system of Clause 35, wherein analyzing the electrical signals to detect brain activity data comprises filtering the electrical signals to reduce a contribution of electrical signals generated from heart activity.
37. The system of Clause 35, wherein analyzing the electrical signals to detect brain activity data comprises filtering the electrical signals to reduce a contribution of electrical signals generated from muscle activity.
38. The system of any one of the Clauses herein, wherein the physiological data comprises motion data, and wherein the computing device is further configured to analyze the motion data to make a fall determination.
39. The system of any one of the Clauses herein, wherein providing the patient stroke indicator includes classifying an identified stroke as ischemic or hemorrhagic.
40. The system of any one of the Clauses herein, wherein providing the patient stroke indicator includes determining whether a patient has suffered a stroke.
41. The system of any one of the preceding Clauses, wherein providing the patient stroke indicator includes determining a risk that a patient will suffer a stroke.
42. The system of any one of the Clauses herein, wherein providing the patient stroke indicator includes determining a location of the stroke.
43. The system of any one of the Clauses herein, wherein providing the patient stroke indicator includes providing a confidence score associated with a determination of patient stroke.
44. The system of any one of the Clauses herein, wherein providing the patient stroke indicator includes providing recommended therapeutic action accompanying a stroke determination.
45. A device comprising:
at least one housing configured to be disposed at a rear portion of a patient's neck or skull base; and
a plurality of electrodes carried by the housing, the electrodes configured to detect electrical signals corresponding to brain activity in at least the P3, Pz, and P4 brain regions of the patient.
46. The device of Clause 45, wherein the device further comprises processing circuitry configured to analyze the detected electrical signals to provide a patient stroke indicator.
47. The device of Clause 46, wherein the processing circuitry comprises a tensor processing unit.
48. The device of any one of the Clauses herein, wherein the device is configured to be implanted.
49. The device of Clause 48, wherein the device is configured to be implanted subcutaneously.
50. The device of any one of the Clauses herein, wherein the device is configured to be disposed over the patient's skin.
51. The device of any one of the Clauses herein, wherein the device is configured to be disposed above the patient's shoulders.
52. The device of any one of the Clauses herein, wherein the device is configured to be disposed at or below the patient's occipital bone.
53. The device of any one of the Clauses herein, wherein the electrodes are configured to contact the patient's skin.
54. The device of Clause 53, wherein the electrodes include protrusions configured to at least partially penetrate the patient's skin.
55. The device of Clause 54, wherein the protrusions comprise microneedles.
56. The device of any one of the Clauses herein, wherein the housing has a volume of less than about 1.5 cc, about 1.4 cc, about 1.3 cc, about 1.2 cc, about 1.1 cc, about 1.0 cc, about 0.9 cc, about 0.8 cc, about 0.7 cc, about 0.6 cc, about 0.5 cc, or about 0.4 cc.

57. The device of any one of the Clauses herein, wherein the housing has a lower surface configured to face towards the patient's tissue for sensing, an upper surface opposite the lower surface, and a thickness extending between the lower surface and the upper surface.
58. The device of Clause 57, wherein the thickness is less than about 10 mm, about 9 mm, about 8 mm, about 7 mm, about 6 mm, about 5 mm, about 4 mm, or about 3 mm.
59. The device of Clause 57 or 58, wherein the electrodes are exposed along the lower surface.
60. The device of any one of the Clauses herein, wherein at least three electrodes are exposed along the lower surface, and wherein the three electrodes are not aligned along a common axis.
61. The device of Clause 60, wherein the housing is elongated along a horizontal axis, and wherein a first electrode is disposed substantially centrally along the horizontal axis, a second electrode is spaced apart from the first electrode along the horizontal axis in a first direction, and wherein the third electrode is spaced apart from the first electrode along the horizontal axis in a second direction opposite the first.
62. The device of Clause 61, wherein the housing is elongated along a first horizontal axis, and wherein a first electrode is disposed substantially centrally along the horizontal axis, a second electrode is disposed towards a first end portion of the housing along the horizontal axis.
63. The device of any one of the Clauses herein, wherein the upper and lower surface form a substantially boomerang or chevron shape.
64. The device of any one of the Clauses herein, wherein one or more electrodes are disposed on a first major surface of the device and one or more electrodes are disposed on a second, opposite major surface of the device.
65. The device of any one of the Clauses herein, wherein one or more electrodes are disposed on a first surface of the device and one or more electrodes are disposed on a second, opposite surface of the device.
66. The device of any one of the Clauses herein, wherein the device is configured to be delivered to a target site through a trocar introducer.
67. A method for detecting and/or predicting strokes, the method comprising:
obtaining physiological data from a patient via a sensor device;
analyzing the physiological data; and
based on the analyses, providing a patient stroke indicator.
68. The method of any one of the Clauses herein, wherein the sensor device comprises a device of any one of the preceding Clauses.
69. The method of any one of the Clauses herein, wherein obtaining the physiological data comprises detecting brain activity data.
70. The method of any one of the Clauses herein, wherein obtaining physiological data comprises detecting electrical activity via electrodes of the sensor device, the electrical activity corresponding to activity in at least one of the P3, Pz, and P4 brain regions of the patient.
71. The method of any one of the Clauses herein, wherein obtaining physiological data comprises detecting electrical activity via electrodes of the sensor device, the electrical activity corresponding to activity in each of the P3, Pz, and P4 brain regions of the patient.
72. The method of any one of the Clauses herein, wherein obtaining physiological data comprises obtaining the physiological data while the sensor device is disposed at or adjacent a rear portion of the patient's neck or skull base.
73. The method of any one of the Clauses herein, wherein obtaining physiological data comprises obtaining the physiological data while the sensor device is disposed above the patient's shoulders.
74. The method of any one of the Clauses herein, wherein obtaining physiological data comprises obtaining the physiological data while the sensor device is disposed at or below the patient's occipital bone.
75. The method of any one of the Clauses herein, wherein obtaining physiological data comprises obtaining the physiological data while the sensor device is implanted within the patient subcutaneously.
76. The method of any one of Clauses 67-75, wherein obtaining the physiological data further comprises obtaining additional physiological data from the patient with one or more additional sensor devices, including at least one of: an accelerometer, a heart rate monitor, a blood pressure monitor, a respiration monitor, an electrocardiography (ECG) sensor, a galvanic skin sensor, or a thermometer.
77. The method of any one of the Clauses herein, wherein obtaining physiological data from the patient comprises:
providing a prompt for the patient to perform one or more actions; and
recording patient physiological data while the patient attempts to perform the one or more actions.
78. The method of any one of the Clauses herein, wherein the one or more actions comprises at least one of: lifting a limb, moving a hand or fingers, speaking, blinking, or making a facial expression.
79. The method of any one of the Clauses herein, wherein providing the patient stroke indicator includes classifying an identified stroke as ischemic or hemorrhagic.
80. The method of any one of the Clauses herein, wherein providing the patient stroke indicator includes determining whether a patient has suffered a stroke.
81. The method of any one of the Clauses herein, wherein providing the patient stroke indicator includes determining a risk that a patient will suffer a stroke.
82. The method of any one of the Clauses herein, wherein providing the patient stroke indicator includes determining a location of the stroke.
83. The method of any one of the Clauses herein, wherein providing the patient stroke indicator includes providing a confidence score associated with a determination of patient stroke.
84. The method of any one of the Clauses herein, wherein providing the patient stroke indicator includes providing recommended therapeutic action accompanying a stroke determination.
85. The method of any one of the Clauses herein, wherein providing the patient stroke indicator comprises transmitting an alert to an emergency healthcare provider.
86. A non-transitory computer-readable medium storing instructions that, when executed by one or more processors of a computing device, cause the computing device to perform operations comprising:
the method of any one of the preceding Clauses.

87. A computing device comprising:
one or more processors; and
the non-transitory computer-readable medium of Clause 79.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
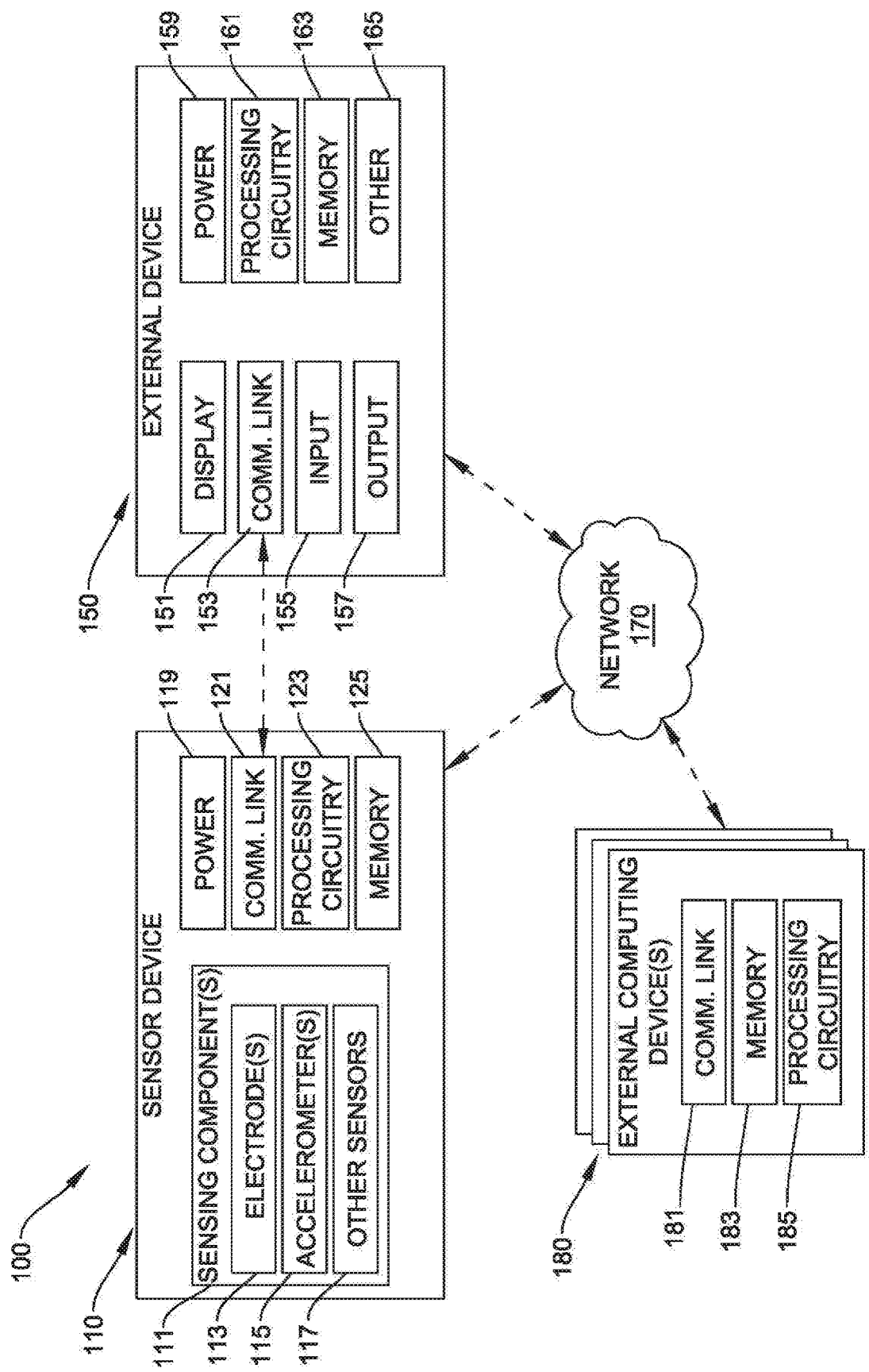
FIG. 1 is a schematic diagram of a stroke detection system configured in accordance with embodiments of the present technology.

It can be difficult to determine whether a patient is suffering from a stroke or has suffered from a stroke. Current diagnostic techniques typically involve evaluating a patient for visible symptoms, such as paralysis or numbness of the face, arm, or leg, as well as difficultly walking, speaking, or understanding. However, these techniques may result in undiagnosed strokes, particularly more minor strokes that leave patients relatively functional upon cursory evaluation. Even for relatively minor strokes, it is important to treat the patient as soon as possible because treatment outcomes for stroke patients are highly time-dependent. Accordingly, there is a need for improved methods for detecting strokes.

Embodiments of the present technology enable detection of strokes by obtaining patient physiological data using a sensor device and analyzing the physiological data to provide a stroke indication, as described in more detail below. For example, a monitoring device can be equipped with electrodes (e.g., electroencephalogram (EEG) electrodes) that can be used to sense and record a patient's brain electrical activity. The monitoring device can be implantable (e.g., subcutaneously) or configured to be disposed over a patient's skin.

Conventional EEG electrodes are typically positioned over a large portion of a user's scalp. While electrodes in this region are well positioned to detect electrical activity from the patient's brain, there are certain drawbacks. Sensors in this location interfere with patient movement and daily activities, making them impractical for prolonged monitoring. Additionally, implanting electrodes under the patient's scalp is difficult and may lead to significant patient discomfort. To address these and other shortcomings of conventional EEG sensors, embodiments of the present technology include a sensor device configured to record electrical signals at a region adjacent a rear portion of the patient's neck or base the patient's skull. In this position, implantation under the patient's skin is relatively simple, and a temporary application of a wearable sensor device (e.g., coupled to a bandage, garment, band, or adhesive member) does not unduly interfere with patient movement and activity.

However, the EEG signals detected via electrodes disposed at or adjacent the back of a patient's neck may be relatively noisy. For example, the electrical signals associated with brain activity may be intermixed with electrical signals associated with cardiac activity (e.g., ECG signals) and muscle activity (e.g., EMG signals) among other artifacts. Accordingly, in some embodiments, the sensor data may be filtered or otherwise manipulated to separate the brain activity data (e.g., EEG signals) from other electrical signals (e.g., ECG signals, EMG signals, etc.).

As described in more detail below, in some embodiments, the sensor data can be analyzed to make a stroke determination includes using a classification algorithm, which can itself be derived using machine learning techniques applied to databases of known stroke patient data. The detection algorithm(s) can be passive (involving measurement of a purely resting patient) or active (involving prompting a patient to perform potentially impaired functionality, such as moving particular muscle groups (e.g., raising an arm, moving a finger, moving facial muscles, etc.,) and/or speaking while recording the electrical response).

Example Systems

The following discussion provides a brief, general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a schematic diagram of system 100 configured in accordance with an embodiment of the disclosed technology. Although the system 100 is shown with certain devices for purposes of explanation, in various examples any one or more of the devices shown in FIG. 1 can be omitted. Similarly, although the devices shown in FIG. 1 are illustrated as including certain components, in various examples any one or more of the particular components within these devices can be omitted (e.g., the sensor device 110 may omit the accelerometer 115). Moreover, any of the devices can include additional components not specifically shown here.

The system 100 can be configured to sense physiological patient data and analyze that data to make a stroke determination. In an example, the system 100 includes a sensor device 110 that is configured to be implanted in a target site of the patient or disposed over the skin of the patient at a target site. The sensor device may be a relatively small device, and may be placed (e.g., inserted) under or over the skin at the back of the patient's neck or base of the skull. As described in more detail below, the sensor device 110 can detect one more physiological parameters of a patient (e.g., electrical activity corresponding to brain activity in particular regions of the patient's brain, heart rhythm data, motion data, etc.). The sensor device 110 can be communicatively coupled to an external device 150, for example via a wireless connection. In some embodiments, the external device 150 can be a mobile device (e.g., a smartphone, tablet, smartwatch, etc.) or other computing device with which the patient can interact. In operation, the patient may receive output or instructions from the external device 150 that are based at least in part on data received at the external device 150 from the sensor device 110. For example, the external device 150 may provide an alert to the patient or another entity (e.g., a call center) based on a stroke indication provided by the sensor device 110. Additionally or alternatively, the external device 150 may output user prompts which can be synchronized with data collection via the sensor device 110. For example, the external device 150 may instruct the user to lift an arm, make a facial expression, etc., and the sensor device 110 may record physiological data while the user performs the requested actions. Moreover, the external device 150 may itself analyze the patient (e.g., the patient's activity or condition in response to such prompts), for example using a camera to detect facial drooping, using a microphone to detect slurred speech, or to detect any other indicia of stroke. In some embodiments, such indicia can be compared against pre-stroke inputs (e.g., a stored baseline facial image or voice-print with baseline speech recording).

The sensor device 110 and/or the external device 150 can also be communicatively coupled with one or more external computing devices 180 (e.g., over network 170). In some examples, the external computing devices 180 can take the form of servers, personal computers, tablet computers or other computing devices associated with one or more healthcare providers (e.g., hospitals, medical data analytic companies, device manufacturers, etc.). These external computing devices 180 can collect data recorded by the sensor device 110 and/or the external device 150. In some embodiments, such data can be anonymized and aggregated to perform large-scale analysis (e.g., using machine-learning techniques or other suitable data analysis techniques) to develop and improve stroke detection algorithms using data collected by a large number of sensor devices 110. Additionally, the external computing devices 180 may transmit data to the external device 150 and/or the sensor device 110. For example, an updated algorithm for making stroke determinations may be developed by the external computing devices 180 (e.g., using machine learning or other techniques) and then provided to the sensor device 110 and/or the external device 150 via the network (e.g., as an over-the-air update), and installed on the sensor device 110 and/or external device 150.

In some embodiments, the system 100 can also include additional implantable devices, such as an implantable cardiac monitors, an implantable pacemaker, an implantable cardiac defibrillator, a cardiac resynchronization therapy (CRT) device (e.g., CRT-D defibrillator or CRT-P pacemaker), a neurostimulator, a deep-brain stimulation device, a nerve stimulator, a drug pump (e.g., an insulin pump), a glucose monitor, or other devices. Other devices that may support and enhance a personal ecosystem to reduce stroke risk include fitness monitors, nutrition devices, etc. Additionally or alternatively, a stroke detection device can be used in conjunction with other disease therapies with high risk of stroke as an adverse event (e.g., LVAD devices, TAVI/TAMR devices, bariatric/gastric surgery, etc.)

As noted previously, the sensor device 110 is configured to be coupled to a patient for recording physiological data relevant to a stroke determination. For example, the sensor device 110 can be implanted within the body of a patient, may be disposed directly over a patient's skin (e.g., held in place via an adhesive or fastener), or may be removably worn by the patient. The sensor device 110 includes sensing components 111, which can include a number of different sensors and/or types of sensors. For example, the sensing components 111 can include a plurality of electrodes 113, an accelerometer 115, and optionally other sensors 117. Examples of other sensors 117 include a blood pressure sensor, a pulse oximeter, an ECG sensor or other heart-recording device, an EMG sensor or other muscle-activity recording device, a temperature sensor, a skin galvanometer, hygrometer, altimeter, gyroscope, magnetometer, proximity sensor, hall effect sensors, or any other suitable sensor for monitoring physiological characteristics of the patient. These particular sensing components 111 are exemplary, and in various embodiments the sensors employed can vary.

The electrodes 113 can be configured to detect electrical activity such as brain activity (e.g., EEG data), heart activity (e.g., ECG data), and/or muscle activity (e.g., EMG data). The electrodes 113 may be formed from any suitable conductive material or materials to enable the electrodes to perform electrical measurements on the patient. In some embodiments, the sensor device 110 can be configured to analyze data from the electrodes 113 to extract both brain activity data (e.g., EEG signals) and heart activity data (e.g., ECG signals). The brain activity data may be evaluated to provide a stroke determination or other assessment of brain condition, while the heart activity data may be evaluated to provide an assessment of heart condition or to detect certain cardiac events (e.g., heart rate variability, arrhythmias (e.g., tachyarrhythmias or bradycardia), ventricular or atrial fibrillation episodes, etc.

In some embodiments, the sensor device 110 is configured to analyze data from the electrodes 113 to extract brain activity data and to discard or reduce any contribution from heart or muscle activity. In some embodiments, the electrodes 113 are configured to be disposed over the patient's skin. In such embodiments, the electrodes 113 can include protrusions (e.g., microneedles or other suitable structures) configured to at least partially penetrate the patient's skin so as to improve detection of subcutaneous electrical activity. In some embodiments, the sensor device 110 can be configured to be implanted within the body (e.g., subcutaneously), and as such the electrodes 113 can include a conductive surface exposed along at least a portion of the sensor device 110 so as to detect electrical activity within the body.

The sensor device 110 may be configured to calculate physiological characteristics relating to one or more electrical signals received from the electrodes 113. For example, the sensor device 110 may be configured to algorithmically determine the presence or absence of a stroke or other neurological condition from the electrical signal. In certain embodiments, the sensor device 110 may make a stroke determination for each electrode 113 (e.g., channel) or may make a stroke determination using electrical signals acquired from two or more selected electrodes 113.

In various embodiments, the number and configuration of electrodes 113 can vary. For example, the sensor device 110 can include at least 2, at least 3, at least 4, at least 5, or more electrodes 113 in an array. In some embodiments, the sensor device 110 includes fewer than 6, fewer than 5, fewer than 4, or fewer than 3 electrodes 113 in an array. As described in more detail below, although conventional EEG arrays include a large number of electrodes disposed over the top of a patient's head, some embodiments of the present technology include a relatively small number of electrodes (e.g., three electrodes) configured to be placed over the back of the patient's neck or base of the skull. In this position, electrical data collected via these electrodes 113 may correspond to brain activity in regions determined to be of interest for stroke determination (e.g., the P3, Pz, and/or P4 regions).

In some embodiments, the electrodes 113 may all reside within a single housing of the sensor device 110. In some embodiments, the electrodes 113 may extend away from a housing of the sensor device 110 and be connected via leads or other connective components. For example, the sensor device 110 can include a housing that encompasses certain components (e.g., the power 119, communications link 121, processing circuitry 123, and/or memory 125), and the electrodes 113 (and/or other sensing components 111) can be coupled to the housing via electrical leads or other suitable connections. In such configurations, the electrodes 113 can be positioned at locations spaced apart from the housing of the sensor device 110. In some embodiments, the electrodes 113 can be disposed within discrete housings that are in turn coupled to a housing containing the other components of the sensor device 110. Such a configuration, in which multiple housings (or sub-housings) are coupled together via flexible or other connectors, may facilitate placement of the sensor device 110 at a desired location to improve patient comfort. Additionally, this may facilitate placement of electrodes 113 at desirable positions for detecting clinically useful brain activity data.

The accelerometer 115 can be configured to detect patient movement. In some embodiments, patient movement data collected via the accelerometer 115 can be used to make a fall determination. Fall detection can be particularly valuable when assessing potential stroke patients, as a large percentage of patients admitted for ischemic or hemorrhagic stroke have been found to have had a significant fall within 15 days of the stroke event. Accordingly, in some embodiments, the sensor device 110 can be configured to initiate monitoring of brain activity via the electrodes 113 upon fall detection using the accelerometer 115. In some embodiments, the sensing performed via the electrodes 113 can be modified in response to a fall determination, for example with an increased sampling rate or other modification. In addition to fall detection, the accelerometer 115 (or similar sensor) can be used to determine potential body trauma due to sudden acceleration and/or deceleration (e.g., a vehicular accident, sports collision, concussion, etc.). These events could be thrombolytic, a precursor to stroke.

The sensor device 110 can also include a power source 119 (e.g., a battery, capacitors). In some embodiments, the power source 119 can be rechargeable, for example using inductive charging or other wireless charging techniques. Such rechargeability can facilitate long-term placement of the sensor device 110 on or within a patient.

A communications link 121 enables the sensor device 110 to transmit to and/or receive data from external devices (e.g., external device 150 or external computing devices 180). The communications link 121 can include a wired communication link and/or a wireless communication link (e.g., Bluetooth, Near-Field Communications, LTE, 5G, Wi-Fi, infrared and/or another wireless radio transmission network).

The processing circuitry 123 can include one or more CPUs, ASICs, digital signal processing circuitry, or any other suitable electrical components configured to process data from the sensing components 111 and control operation of the sensor device 110. In some embodiments, the processing circuitry 123 includes hardware particularly adapted for artificially intelligence and/or machine learning applications, for example, a tensor processing unit (TPU) or other such hardware. In certain embodiments, the processing circuitry of the sensor device 110 may include one or more input protection circuits to filter the electrical signals and may include amplifier/filter circuitry to remove DC and high frequency components, one or more analog-to-digital (A/D) converters, or any other suitable components.

The sensor device 110 can further include memory 125, which can take the form of one or more computer readable storage modules configured to store information (e.g., signal data, subject information or profiles, environmental data, data collected from one or more sensing components, media files) and/or executable instructions that can be executed by the processing circuitry 123. The memory 125 can include, for example, instructions for analyzing patient data to determine whether a patient is undergoing or has recently or previously undergone a stroke. In some embodiments, the memory 125 stores data (e.g., signal data acquired from the sensing components 111) used in the stroke detection techniques disclosed herein.

As noted above, in some embodiments, the sensor device 110 may also communicate with an external device 150. The external device 150 can be, for example, a smartwatch, smartphone, laptop, tablet, desktop PC, or any other suitable computing device and can include one or more features, applications and/or other elements commonly found in such devices. For example, the external device 150 can include display 151, a communications link 153 (e.g., a wireless transceiver that may include one or more antennas for wirelessly communicating with, for example, other devices, websites, and the sensor device 110). Communication between the external device 150 and other devices can be performed via, e.g., a network 170 (which can include the Internet, public and private intranet, a local or extended Wi-Fi network, cell towers, the plain old telephone system (POTS), etc.), direct wireless communication, etc. The external device 150 can additionally include well-known input components 131 and output components 133, including, for example, a touch screen, a keypad, speakers, a camera, etc.

In operation, the patient may receive output or instructions from the external device 150 that are based at least in part on data received at the external device 150 from the sensor device 110. For example, the sensor device 110 may generate a stroke indication based on analysis of data collected via sensing components 111. The sensor device 110 may then instruct the external device 150 to output an alert to the patient (e.g., via display 151 and/or output 157) or another entity. In some embodiments, the alert can both be displayed to the user (e.g., via display 151 of the external device) and can also be transmitted to an appropriate emergency medical response service (e.g., a 9-1-1 call may be placed with location data from the external device 150 used to direct responders to locate the patient), and/or to other healthcare provider entities or individuals (e.g. a hospital, emergency room, or physician). In some embodiments, embedded circuitry that provides location data (e.g., a GPS unit) can be included within the sensor device 110.

Additionally or alternatively, the external device 150 may output user prompts which may be used in conjunction with physiological data collection via the sensor device 110. For example, the external device 150 may instruct the user to perform an action (e.g., lift an arm, make a facial expression, etc.), and the sensor device 150 may record physiological data while the user performs the requested actions. In some embodiments, the external device 150 may itself analyze physiological parameters of the patient, for example using a camera to detect facial drooping or other indicia of stroke. In some embodiments, such physiological data collected via the external device 150 can be combined with data collected via the sensing components 111 and analyzed together to make a stroke determination.

As noted previously, the external computing device(s) 180 can take the form of servers or other computing devices associated with healthcare providers or other entities. The external devices can include a communications link 181 (e.g., components to facilitate wired or wireless communication with other devices either directly or via the network 170), a memory 183, and processing circuitry 185. These external computing devices 180 can collect data recorded by the sensor device 110 and/or the external device 150. In some embodiments, such data can be anonymized and aggregated to perform large-scale analysis (e.g., using machine-learning techniques or other suitable data analysis techniques) to develop and improve stroke detection algorithms using data collected by a large number of sensor devices 110 associated with a large population of patients. Additionally, the external computing devices 180 may transmit data to the external device 150 and/or the sensor device 110. For example, an updated algorithm for making stroke determinations may be developed by the external computing devices 180 (e.g., using machine learning or other techniques) and then provided to the sensor device 110 and/or the external device 150 via the network 170, and installed on the recipient device 110/150.

Example Sensor Devices

Figure 2A:
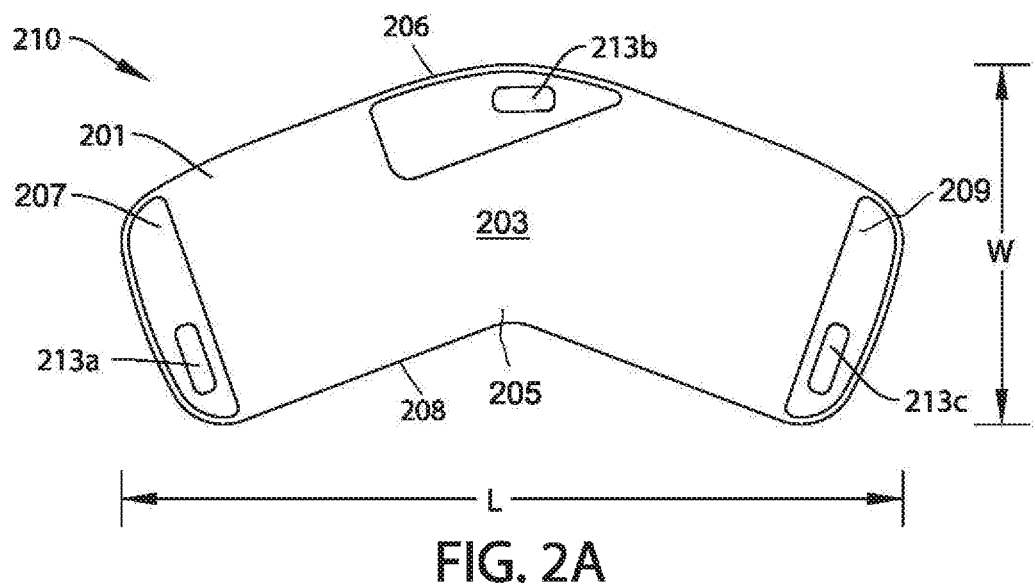
FIG. 2A depicts a top view of a sensor device in accordance with embodiments of the present technology.

FIG. 2A illustrates a plan view of an example sensor device 210. In some embodiments, the sensor device 210 can include some or all of the features of the sensor device 110 described above with respect to FIG. 1 and/or the sensor device 310 described below with respect to FIG. 3, and can include additional features as described in connection with FIG. 2A. In the illustrated example, the sensor device 210 includes a housing 201 that carries a plurality of electrodes 213a-c (collectively "electrodes 213") therein. In operation, the electrodes 213a-c can be placed in direct contact with tissue at the target site (e.g., with the user's skin if placed over the user's skin, or with subcutaneous tissue if the sensor device 210 is implanted). The housing 201 additionally encloses electronic circuitry located inside the sensor device 210 and protects the circuitry contained therein from body fluids. In various embodiments, the electrodes 213 can be disposed along any surface of the sensor device 210 (e.g., anterior surface, posterior surface, left lateral surface, right lateral surface, superior side surface, inferior side surface, or otherwise), and the surface in turn may take any suitable form.

Figure 2B:
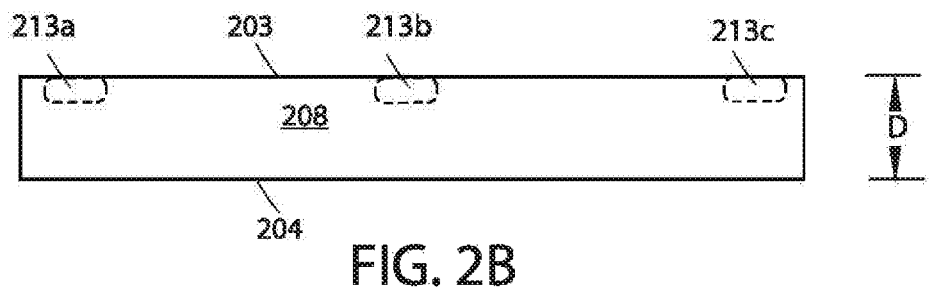
FIG. 2B depicts a side view of the sensor device shown in FIG. 2A in accordance with the present technology.

In the example of FIGS. 2A and 2B, the housing 201 can be a biocompatible material having a relatively planar shape including a first major surface 203 configured to face towards the tissue of interest (e.g., to face anteriorly when positioned at the back of the patient's neck) a second major surface 204 opposite the first, and a depth D or thickness of the housing 201 extending between the first and second major surfaces. The housing 201 can define a superior side surface 206 (e.g., configured to face superiorly when the device 101 is implanted in or at the patient's neck) and an opposing inferior side surface 208. The housing 201 can further include a central portion 205, a first lateral portion (or left portion) 207, and a second lateral portion (or right portion) 209. The electrodes 213 are distributed about the housing 201 such that a central electrode 213b is disposed within the central portion 205 (e.g., substantially centrally along a horizontal axis of the device), a left electrode 213a electrode is disposed within the left portion 207, and a right electrode 213c is disposed within the right portion 209. As illustrated, the housing 201 can define a boomerang or chevron-like shape in which the central portion 205 includes a vertex, with the first and second lateral portions 207 and 209 extending both laterally outward and from the central portion 205 and also at a downward angle with respect to a horizontal axis of the device.

The configuration of the housing 201 can facilitate placement either over the user's skin in a bandage-like form or for subcutaneous implantation. As such, a relatively thin housing 201 can be advantageous. Additionally, the housing 201 can be flexible in some embodiments, so that the housing 201 can at least partially bend to correspond to the anatomy of the patient's neck (e.g., with left and right lateral portions 207 and 209 of the housing 201 bending anteriorly relative to the central portion 205 of the housing 201).

In some embodiments, the housing 201 can have a length L of between about 15-50 mm, between about 20-30 mm, or about 25 mm. The housing 201 can have a width W of between about 2.5-15 mm, between about 5-10 mm, or about 7.5 mm. In some embodiments, the housing 201 can have a thickness of the thickness is less than about 10 mm, about 9 mm, about 8 mm, about 7 mm, about 6 mm, about 5 mm, about 4 mm, or about 3 mm. In some embodiments, the thickness of the housing 201 can be between about 2-8 mm, between 3-5 mm, or about 4 mm. The housing 201 can have a volume of less than about 1.5 cc, about 1.4 cc, about 1.3 cc, about 1.2 cc, about 1.1 cc, about 1.0 cc, about 0.9 cc, about 0.8 cc, about 0.7 cc, about 0.6 cc, about 0.5 cc, or about 0.4 cc. In some embodiments, the housing 201 can have dimensions suitable for implantation through a trocar introducer or any other suitable implantation technique.

As illustrated, the electrodes 213 carried by the housing 201 are arranged so that all three electrodes 213 do not lie on a common axis. In such a configuration, the electrodes 213 can achieve a better signal vector as compared to electrodes that are all aligned along a single axis. This can be particularly useful in a sensor device 210 configured to be implanted at the neck while detecting electrical activity in the brain. In some embodiments, this electrode configuration also provides for improved cardiac ECG sensitivity by integrating 3 potential signal vectors.

In the example shown in FIG. 2, all three electrodes 213 are located on the first major surface 203 and are substantially flat and outwardly facing. However, in other examples one or more electrodes 213 may utilize a three-dimensional configuration (e.g., curved around an edge of the device 210). Similarly, in other examples one or more electrodes 213 may be disposed on the second major surface opposite the first. The various electrode configurations allow for configurations in which electrodes 213 are located on both the first major surface and the second major surface. In other configurations, such as that shown in FIG. 2, electrodes 213 are only disposed on one of the major surfaces of the housing 201. The electrodes 213 may be formed of a plurality of different types of biocompatible conductive material (e.g., stainless steel, titanium, platinum, iridium, or alloys thereof), and may utilize one or more coatings such as titanium nitride or fractal titanium nitride. In some embodiments, the material choice for electrodes can also include materials having a high surface area (e.g., to provide better electrode capacitance for better sensitivity) and roughness (e.g., to aid implant stability). Although the example shown in FIG. 2 includes three electrodes 213, in some embodiments the sensor device 210 can include 1, 2, 4, 5, 6, or more electrodes carried by the housing 201.

Figure 2C:
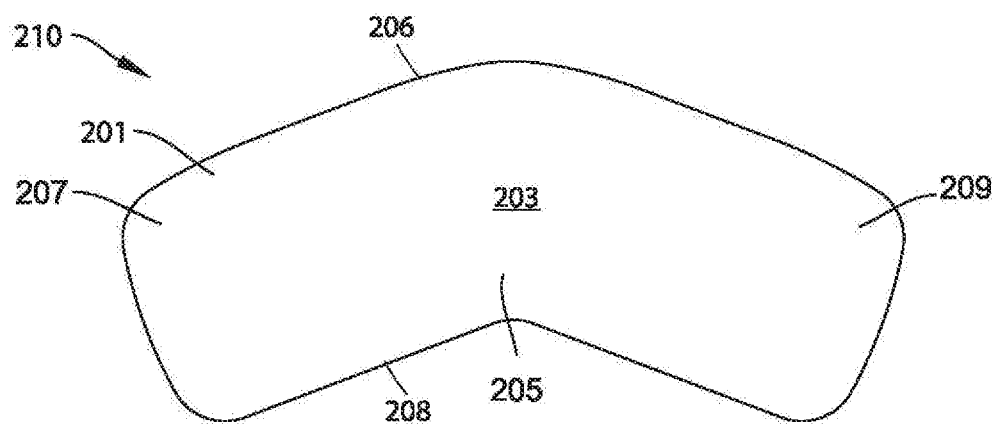
FIG. 2C depicts a top view of another embodiment of sensor device in accordance with the present technology.
Figure 2D:
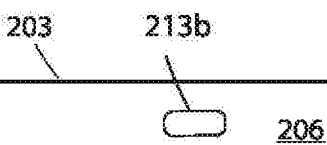
FIG. 2D depicts a side view of another embodiment of a sensor device in accordance with the present technology.
Figure 2E:
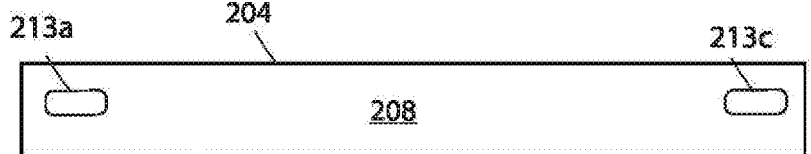
FIG. 2E depicts a side view of another embodiment of a sensor device in accordance with the present technology.
Figure 2F:
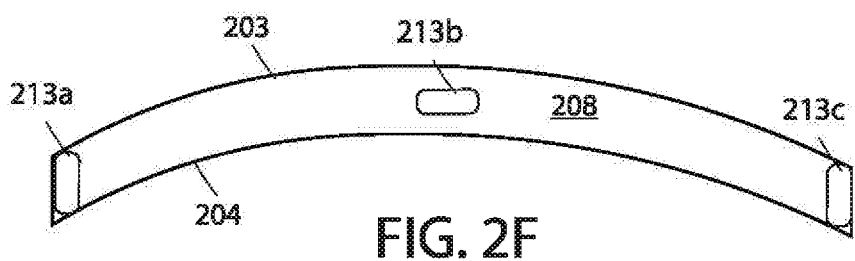
FIG. 2F depicts a side view of another embodiment of a sensor device in accordance with the present technology.

FIG. 2C illustrates another example embodiment in which the electrodes 213 are not exposed along the first major surface 203 of the housing 201. Instead, the electrodes 213 can be exposed along superior and inferior side surfaces (e.g., facing superiorly and inferiorly when implanted at or on a patient's neck), as shown in FIGS. 2d and 2E. FIG. 2F illustrates another example in which the housing 201 assumes a curved configuration, and in which the electrodes can be place along the superior and/or inferior side surfaces of the housing 201. In some embodiments, a curved configuration can improve patient comfort and more readily conform to the anatomy of the patient's neck region.

In operation, the electrodes 213 are used to sense electrical signals (e.g., EEG signals) which may be submuscular or subcutaneous. The sensed electrical signals may be stored in a memory of the sensor device 210, and signal data may be transmitted via a communications link to another device (e.g., external device 150 of FIG. 1). The sensed electrical signals may be time-coded or otherwise correlated with time data, and stored in this form, so that the recency, frequency, time of day, time span, or date(s) of a particular signal data point or data series (or computed measures or statistics based thereon) may be determined and/or reported. In some examples, electrodes 213 may additionally or alternatively be used for sensing any bio-potential signal of interest, such as an electrocardiogram (ECG), intracardiac electrogram (EGM), electromyogram (EMG), or a nerve signal, from any implanted location. These data may be time-coded or time-correlated, and stored in that form, in the manner described above with respect to EEG signal data.

Figure 3:
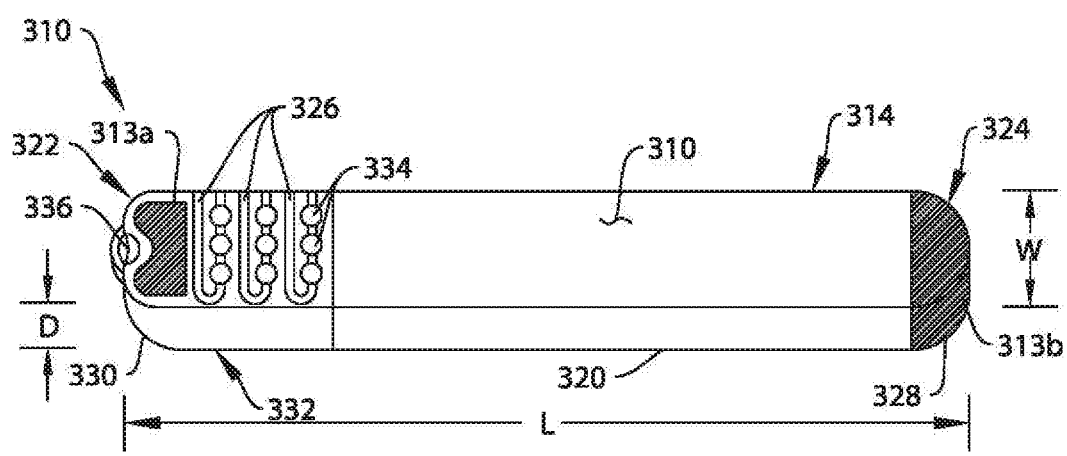
FIG. 3 depicts another sensor device in accordance with embodiments of the present technology.

FIG. 3 illustrates another example sensor device 310. In some embodiments, the sensor device 310 can include some or all of the features of the sensor devices 110 and 210 described above with respect to FIGS. 1 and 2 in accordance with embodiments of the present technology, and can include additional features as described in connection with FIG. 3. In the example shown in FIG. 3, sensor device 310 may be embodied as a monitoring device having housing 314, proximal electrode 313a and distal electrode 313b (individually or collectively "electrode 313" or "electrodes 313"). Housing 314 may further comprise first major surface 318, second major surface 320, proximal end 322, and distal end 324. Housing 314 encloses electronic circuitry located inside the sensor device 310 and protects the circuitry contained therein from body fluids. Electrical feedthroughs provide electrical connection of electrodes 313. In an example, sensor device 310 may be embodied as an external monitor, such as patch that may be positioned on an external surface of the patient, or another type of medical device (e.g., instead of as an ICM), such as described further herein.

In the example shown in FIG. 3, sensor device 310 is defined by a length "L," a width "W," and thickness or depth "D." sensor device 310 may be in the form of an elongated rectangular prism wherein the length L is significantly larger than the width W, which in turn is larger than the depth D. In one example, the geometry of the sensor device 310—in particular, a width W being greater than the depth D—is selected to allow sensor device 310 to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 313a and distal electrode 313b may range from 30 millimeters (mm) to 55 mm, 35 mm to 55 mm, and from 40 mm to 55 mm and may be any range or individual spacing from 25 mm to 60 mm. In-some examples, the length L may be from 30 mm to about 70 mm. In other examples, the length L may range from 40 mm to 60 mm, 45 mm to 60 mm and may be any length or range of lengths between about 30 mm and about 70 mm. In addition, the width W of first major surface 18 may range from 3 mm to 10 mm and may be any single or range of widths between 3 mm and 10 mm. The thickness of depth D of sensor device 310 may range from 2 mm to 9 mm. In other examples, the depth D of sensor device 310 may range from 2 mm to 5 mm and may be any single or range of depths from 2 mm to 9 mm. In addition, sensor device 310 according to an example of the present disclosure is has a geometry and size designed for ease of implant and patient comfort. Examples of sensor device 310 described in this disclosure may have a volume of 3 cc or less, 2 cc or less, 1 cc or less, 0.9 cc or less, 0.8 cc or less, 0.7 cc or less, 0.6 cc or less, 0.5 cc or less, or 0.4 cc or less, any volume between 3 and 0.4 cc. In addition, in the example shown in FIG. 3, proximal end 322 and distal end 324 are rounded to reduce discomfort and irritation to surrounding tissue once inserted under the skin of the patient.

In the example shown in FIG. 3, once inserted within the patient, the first major surface 318 faces outward, toward the skin of the patient while the second major surface 320 is located opposite the first major surface 318. Consequently, the first and second major surfaces may face in directions along a sagittal axis of patient, and this orientation may be consistently achieved upon implantation due to the dimensions of sensor device 310. Additionally, an accelerometer, or axis of an accelerometer, may be oriented along the sagittal axis.

Proximal electrode 313a and distal electrode 313b are used to sense electrical signals (e.g., EEG signals) which may be submuscular or subcutaneous. Electrical signals may be stored in a memory of the sensor device 310, and signal data may be transmitted via integrated antenna 326 to another medical device, which may be another implantable device or an external device, such as external device 150 (FIG. 1). In some examples, electrodes 313a and 313b may additionally or alternatively be used for sensing any biopotential signal of interest, such as an electrocardiogram (ECG), intracardiac electrogram (EGM), electromyogram (EMG), or a nerve signal, from any implanted location.

In the example shown in FIG. 3, proximal electrode 313a is in close proximity to the proximal end 322, and distal electrode 313b is in close proximity to distal end 324. In this example, distal electrode 313b is not limited to a flattened, outward facing surface, but may extend from first major surface 318 around rounded edges 328 or end surface 330 and onto the second major surface 320 so that the electrode 313b has a three-dimensional curved configuration. In the example shown in FIG. 3, proximal electrode 313a is located on first major surface 318 and is substantially flat, outward facing. However, in other examples proximal electrode 313a may utilize the three-dimensional curved configuration of distal electrode 313b, providing a three-dimensional proximal electrode (not shown in this example). Similarly, in other examples distal electrode 313b may utilize a substantially flat, outward facing electrode located on first major surface 18 similar to that shown with respect to proximal electrode 313a. The various electrode configurations allow for configurations in which proximal electrode 313a and distal electrode 313b are located on both first major surface 18 and second major surface 320. In other configurations, such as that shown in FIG. 3, only one of proximal electrode 313a and distal electrode 313b is located on both major surfaces 318 and 320, and in still other configurations both proximal electrode 313a and distal electrode 313b are located on one of the first major surface 318 or the second major surface 320 (e.g., proximal electrode 313a located on first major surface 318 while distal electrode 313b is located on second major surface 320). In another example, sensor device 310 may include electrodes 313 on both first major surface 318 and second major surface 320 at or near the proximal and distal ends of the device, such that a total of four electrodes 313 are included on sensor device 310. Electrodes 313 may be formed of a plurality of different types of biocompatible conductive material (e.g., stainless steel, titanium, platinum, iridium, or alloys thereof), and may utilize one or more coatings such as titanium nitride or fractal titanium nitride. Although the example shown in FIG. 3 includes two electrodes 313, in some embodiments the sensor device 310 can include 3, 4, 5, or more electrodes carried by the housing 314.

In the example shown in FIG. 3, proximal end 322 includes a header assembly 332 that includes one or more of proximal electrode 313a, integrated antenna 326, anti-migration projections 334, or suture hole 336. Integrated antenna 326 is located on the same major surface (i.e., first major surface 318) as proximal electrode 313a and is also included as part of header assembly 332. Integrated antenna 326 allows sensor device 310 to transmit or receive data. In other examples, integrated antenna 326 may be formed on the opposite major surface as proximal electrode 313a, or may be incorporated within the housing 314 of sensor device 310. In the example shown in FIG. 3, anti-migration projections 334 are located adjacent to integrated antenna 326 and protrude away from first major surface 318 to prevent longitudinal movement of the device. In the example shown in FIG. 3 anti-migration projections 334 includes a plurality (e.g., six or nine) small bumps or protrusions extending away from first major surface 318. As discussed above, in other examples anti-migration projections 334 may be located on the opposite major surface as proximal electrode 313a or integrated antenna 326. In addition, in the example shown in FIG. 3 header assembly 332 includes suture hole 336, which provides another means of securing sensor device 310 to the patient to prevent movement following insert. In the example shown, suture hole 336 is located adjacent to proximal electrode 313a. In one example, header assembly 332 is a molded header assembly made from a polymeric or plastic material, which may be integrated or separable from the main portion of sensor device 310.

Example Methods

Figure 4:
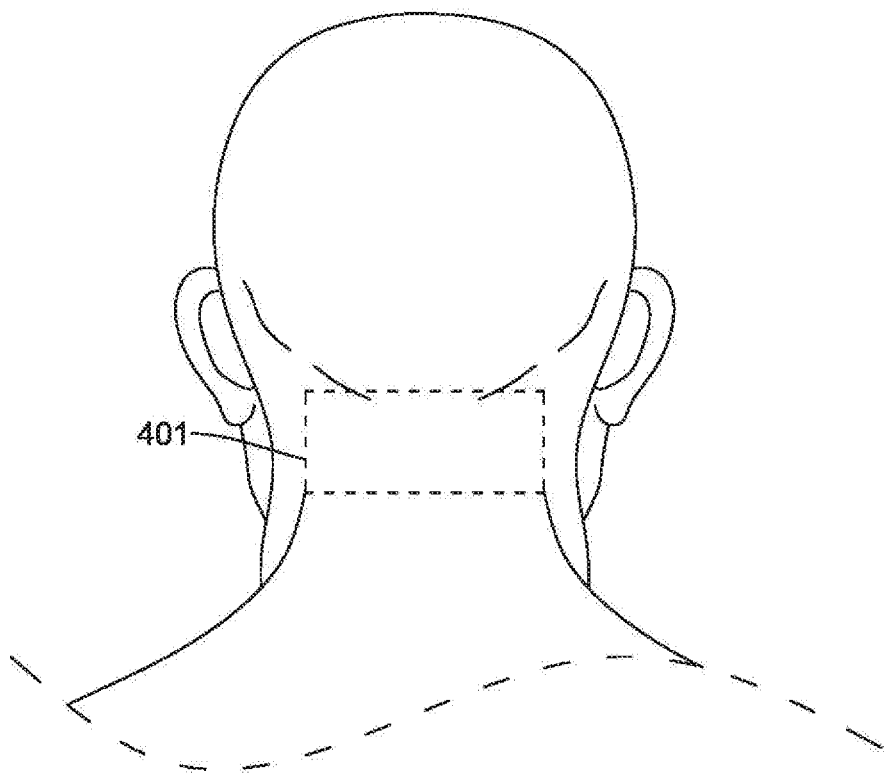
FIG. 4 depicts an exemplary target region for the sensor devices of the present technology.

FIG. 4 illustrates an exemplary target region 401 for positioning a sensor device (e.g., sensor devices 110, 210, 310 described elsewhere herein). As illustrated, the target region 401 can be a rear portion of a user's neck or at the base of the skull. The target region 401 can be positioned above the patient's shoulders and at or below the patient's occipital bone. As noted previously, a sensor device can be disposed in this region either via implantation (e.g., subcutaneously) or by being placed over the patient's skin with one or more electrodes of a sensor device being in direct contact with the patient's skin at or adjacent the target region 401.

Figure 5:
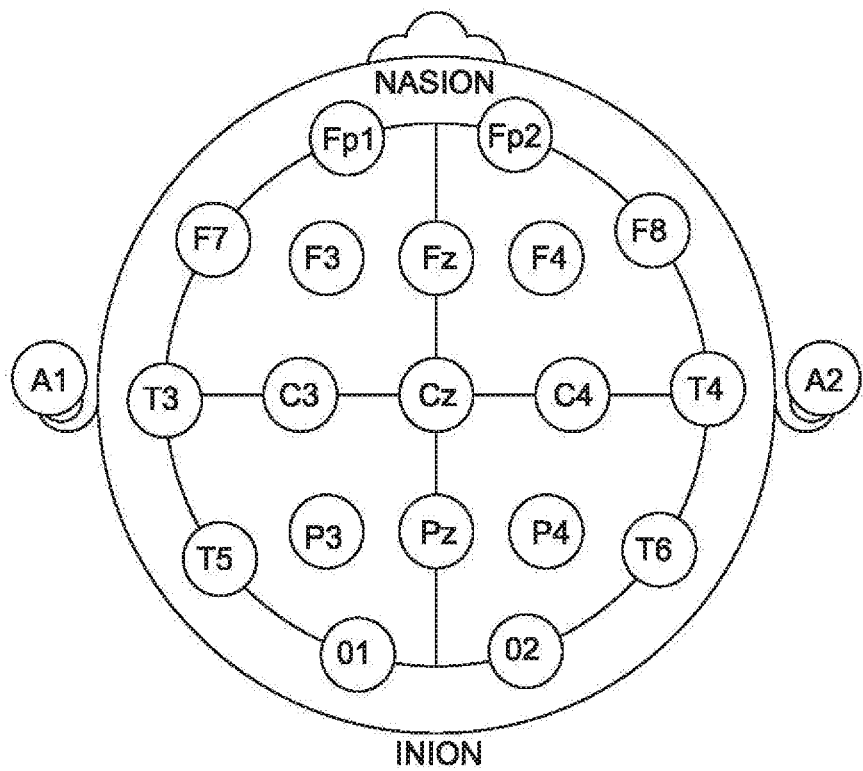
FIG. 5 is a diagram of the 10-20 map for electroencephalography (EEG) sensor measurements.

While conventional EEG electrodes are placed over the patient's scalp, the present technology advantageously enables recording of clinically useful brain activity data via electrodes positioned at the target region 401 at the rear of the patient's neck. This anatomical area is well suited to suited both to implantation of a sensor device and to temporary placement of a sensor device over the patient's skin. In contrast, EEG electrodes positioned over the scalp are cumbersome, and implantation over the patient's skull is challenging and may introduce significant patient discomfort. As noted elsewhere here, conventional EEG electrodes are typically positioned over the scalp to more readily achieve a suitable signal-to-noise ratio for detection of brain activity. However, by using certain digital signal processing, and a special-purpose classifier algorithm, clinically useful brain activity data can be obtained using sensors disposed at the target region 401. Specifically, the electrodes can detect electrical activity that corresponds to brain activity in the P3, Pz, and/or P4 regions (see FIG. 5).

While conventional approaches to stroke detection utilizing EEG have relied on data from a large number of EEG electrodes, the inventors have discovered that clinically useful stroke determinations may be made utilizing relatively few electrodes. In an experiment conducted by the inventors, data from a base set of 56 patients (26 stroke and 30 non-stroke) was used. EEG data was recorded somewhere between 1 and 22 hours post-event using a conventional EEG array with a sampling frequency of 500 Hz over a period of 3 minutes. The EEG data was detrended, then bandpass filtered (e.g., filter 6-40 Hz to remove high-frequency noise), followed re-referencing to Pz, wavelet denoising, and finally low-pass filtering below 25 Hz. With an EEG array of 16 contacts (with Pz serving as ground), and 14 power bins, a total of 224 features were extracted.

Figure 6:
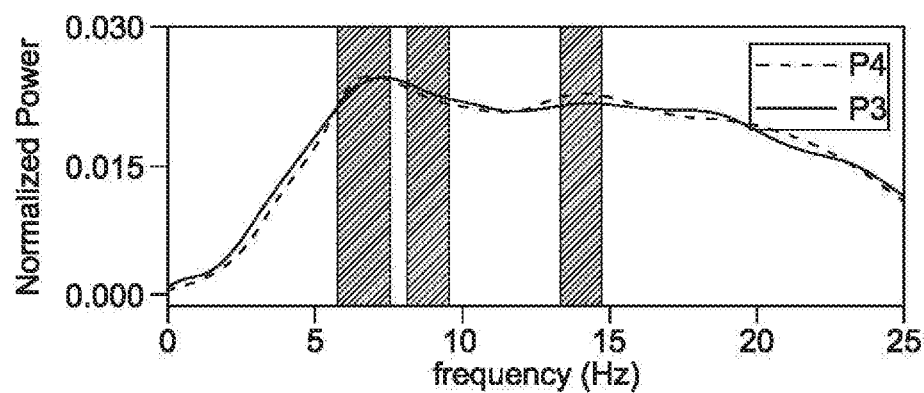
FIG. 6 depicts example EEG spectral power data from a sensor device in accordance with embodiments of the present technology.

A gradient boosting algorithm was trained on the data set following feature extraction to generate a classifier algorithm. The classifier was tuned by paring down features to only those related to the stroke/non-stroke condition. A sequentially backward floating feature selection approach was employed, which sequentially removes individual features using a classifier performance metric. The classifier was further tuned by adjusting the frequency bins. The result of this analysis was five features that effectively discriminate between stroke and non-stroke conditions. These features were three frequency bins associated with the P3 electrode (5.5-7.5 Hz, 8-9.5 Hz, and 13.5-15 Hz) and two frequency bins associated with the P4 electrode (5.5-7.5 Hz and 13.5-15 Hz). FIG. 6 is a graph of normalized power over the relevant frequency bins for the P3 and P4 electrodes. The relevant frequency bins are indicated in the graph with shading.

Figure 7:
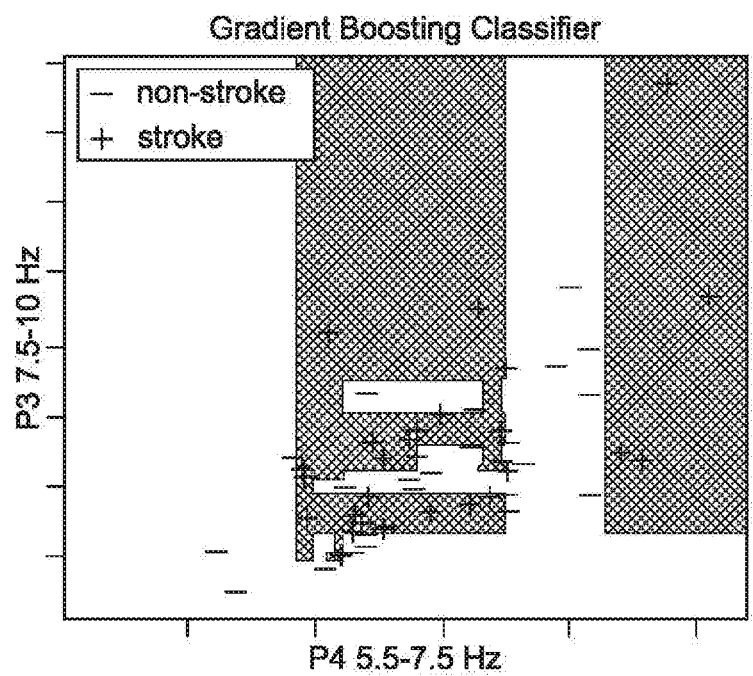
FIG. 7 depicts the output of a gradient boosting classifier for stroke determinations in accordance with embodiments of the present technology.

The resulting classifier succeeded in making stroke/non-stroke determinations with an accuracy of approximately 85%. FIG. 7 graphically illustrates these results mapped using two features (the P4 electrode in the 5.5-7.5 Hz range along the x-axis and the P3 electrode in the 7.5-10 Hz range along the y-axis). The "+" and "−" symbols in the graph reflect the actual stroke/non-stroke condition, and the shaded regions in the graph reflect the predictions made by the classifier. As seen in FIG. 7, the majority of the "+" symbols are grouped within the predicted stroke region and the majority of the "−" symbols are grouped in the predicted non-stroke region. Significantly and surprisingly, this classifier achieved relatively high accuracy while only relying on data from three electrodes: P3, P4, and the ground electrode, Pz. As such, the inventors successfully demonstrated that clinically useful stroke determinations are possible without requiring data from a full array of 16 or more EEG electrodes as found in conventional approaches.

The accuracy of such a classifier can be improved by training the algorithm on larger sets of data corresponding to stroke and non-stroke EEG readings. Additionally, other physiological parameters can be added to the classifier model (e.g., fall detection as determined using an accelerometer, particular heart rhythms, gender, age, medical history, etc.). Additionally, in some embodiments a classifier can be used to discriminate between ischemic and hemorrhagic strokes. Such discrimination can be particularly useful as the interventions may differ. For example, an ischemic stroke may be treated using thrombectomy, while a hemorrhagic stroke may be treated using surgery or another suitable technique.

Figure 8:
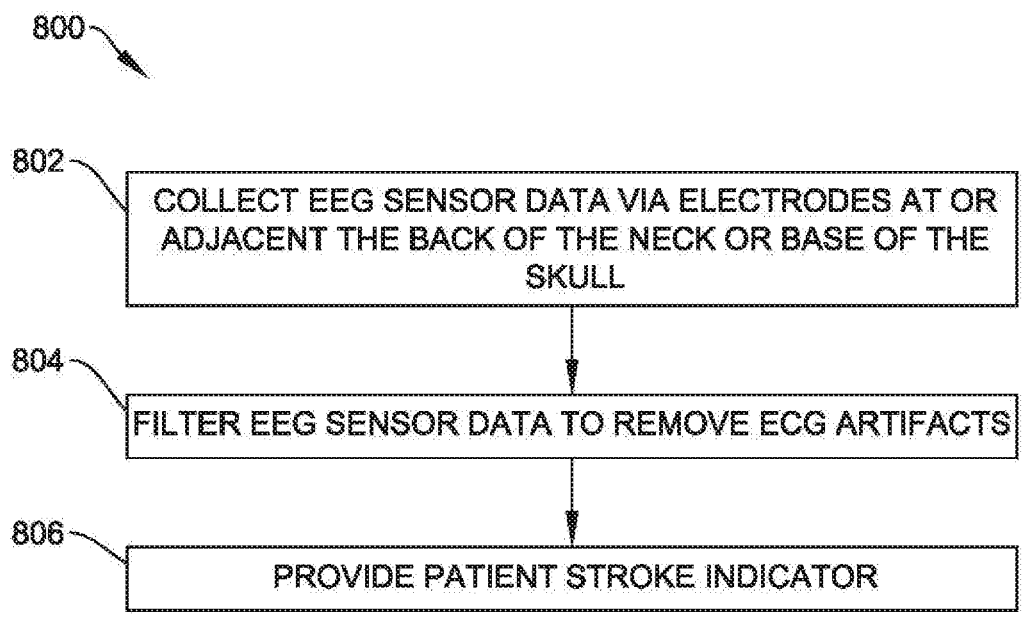
FIG. 8 is a flow diagram of a method for making a stroke determination in accordance with embodiments of the present technology.

FIG. 8 is a flow diagram of a method 800 for making a stroke determination. The process 800 can include instructions stored, for example, in the memory (e.g., memory 125, 163, and/or 183 of FIG. 1) that are executable by the one or more processors (e.g., processing circuitry 123, 161, and/or 185 of FIG. 1). In some embodiments, portions of the process 800 are performed by one or more hardware components (e.g., the sensing components 111 of FIG. 1). In certain embodiments, portions of the process 800 are performed by a device external to the system 100 of FIG. 1.

As illustrated, the process 800 begins in block 802 with collecting EEG sensor data via electrodes disposed at or adjacent the back of the neck or base of the skull (e.g., the target region 401 shown in FIG. 4). In some embodiments, the EEG sensor data can include electrical signals detected using electrodes of a sensor device 110, 210, or 310 as described above with respect to FIGS. 1-3. Such a device can be disposed (e.g., either implanted subcutaneously or positioned over the patient's skin) at the target region 401 (FIG. 4).

The process 800 continues in block 804 with filtering the EEG sensor data to remove ECG artifacts. Conventionally, EEG data has been obtained via electrodes positioned over the scalp because it is a relatively noise-free location for signal acquisition. Other anatomical locations such as back of the neck have not been used, not because EEG signal isn't present, but because of the noisier environment and band-overlap with other physiologic signals such as ECG. However, recent techniques for machine learning/adaptive neural network processing have enhanced the signal extraction capability (e.g., to filter out or reduce the contribution of ECG signals from the EEG signals). One such methodology is described in "ECG Artifact Removal of EEG signal using Adaptive Neural Network" as published in IEEE Xplore 27 May 2019, which is hereby incorporated by reference in its entirety. Similarly, electrical signals associated with muscle activity may also be filtered from the EEG sensor data to remove such artifacts.

In block 806, a patient stroke indicator is provided. The patient stroke indicator can be, for example, a binary output of stroke condition/non-stroke condition, a probabilistic indication of stroke likelihood, or other output relating to the patient's condition and likelihood of having suffered a stroke. This stroke indicator can be calculated using a classifier model as described elsewhere herein. In addition to providing the patient stroke indicator, information or instructions can also be output to a patient or user. The information or instructions can be output via a display device (e.g., the display 151 of FIG. 1). For example, if a stroke is identified in block 806, then the system may provide instructions to route the patient to a comprehensive stroke treatment center or otherwise flag the patient for treatment. In embodiments in which the process 800 is performed while the patient is in an ambulance, the process 800 can output information or instructions to an emergency medical technician (EMT) or other personnel in the rear of the ambulance and/or to the ambulance driver. In some embodiments, the display to the ambulance driver can include navigational information such as a map and instructions to take the patient to a particular hospital or facility with a stroke center.

In some embodiments, prior to, concurrently with, or after providing the stroke indicator in block 806, the method 800 can include triggering an automatic data transmission, for example of a stroke determination which can be output to the patient or another entity (e.g., a call center, emergency response personnel, etc.). A call center may contact the patient or a patient's designated contact to inquire as the patient's status, and/or to confirm a patient stroke. If the patient stroke is confirmed (or if the call center is unable to reach the patient), a 9-1-1 emergency call can be initiated, either manually by call center personnel or automatically.

Figure 9:
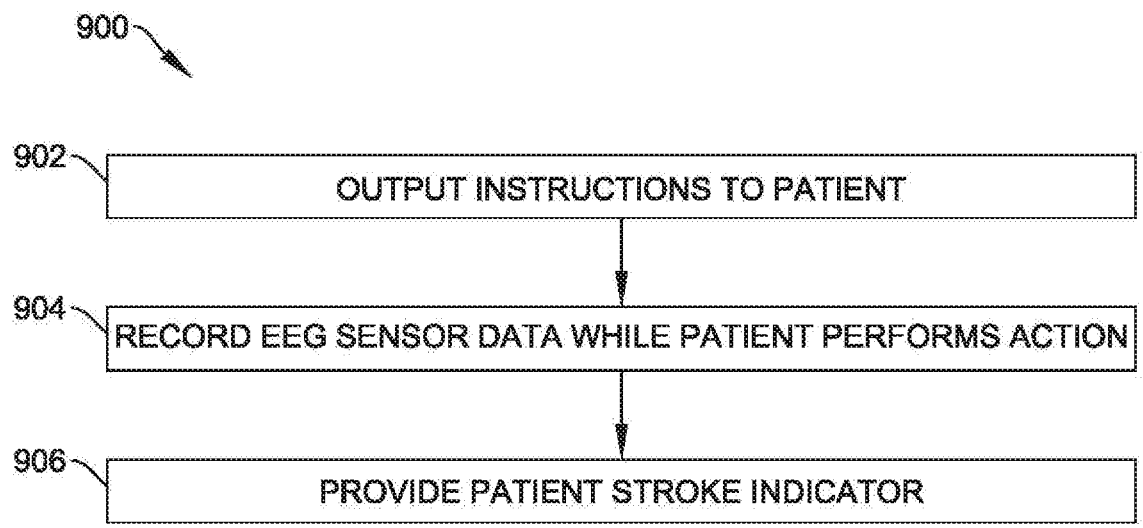
FIG. 9 is a flow diagram of another method for making a stroke determination in accordance with embodiments of the present technology.

FIG. 9 is a flow diagram of another method 900 for making a stroke determination. The process 900 can include instructions stored, for example, in the memory (e.g., memory 125, 163, or 183 of FIG. 1) that are executable by the one or more processors (e.g., processing circuitry 123, 161, or 185 of FIG. 1). In some embodiments, portions of the process 900 are performed by one or more hardware components (e.g., the display 151, input 155, and/or output 157 of the external device 150; the sensing components 111 of the sensor device 110 (FIG. 1)). In certain embodiments, portions of the process 900 are performed by a device external to the system 100 of FIG. 1.

In block 902, instructions are output to a patient to perform an action. For example, instructions may be output via external device 150 (FIG. 1), using a display, speaker, or other suitable output. The instructions can include patient prompts for the patient to perform particular acts or movements, such as lifting an arm or leg, moving a hand or fingers, speaking, smiling, recognition of an image, clapping, etc. In some embodiments, these prompts can be provided in succession, and patient data can be obtained after each prompt while the patient responds (or fails to respond) to the particular instructions. In some embodiments, accelerometer data (e.g., an accelerometer within external device 150) can be used to monitor patient movement in response to the provided prompts.

In block 904, EEG sensor data is collected while the patient performs the actions included in the instructions of block 902. In some embodiments, the EEG sensor data can be collected via electrodes disposed at or adjacent the back of the neck or base of the skull (e.g., the target region 401 shown in FIG. 4) as described elsewhere herein. In some embodiments, the EEG sensor data can include electrical signals detected using electrodes of a sensor device 110, 210, or 310 as described above with respect to FIGS. 1-3. Such a device can be disposed (e.g., either implanted subcutaneously or positioned over the patient's skin) at a target region of the patient.

In block 906, the sensor data is analyzed and, based on the analysis, the system can provide a patient stroke indicator. The analysis can include, for example, using a classifier algorithm as described elsewhere herein. The patient stroke indicator can be, for example, a binary output of stroke condition/non-stroke condition, a probabilistic indication of stroke likelihood, or other output relating to the patient's condition and likelihood of having suffered a stroke. In some embodiments, if a stroke is indicated, the system can output appropriate information or instructions via a display device (e.g., the display 116 of FIG. 1 or the display 34 of FIGS. 2-4). For example, if a stroke is identified in block 906, then the system may provide instructions to route the patient to a comprehensive stroke treatment center or otherwise flag the patient for treatment.

Figure 10:
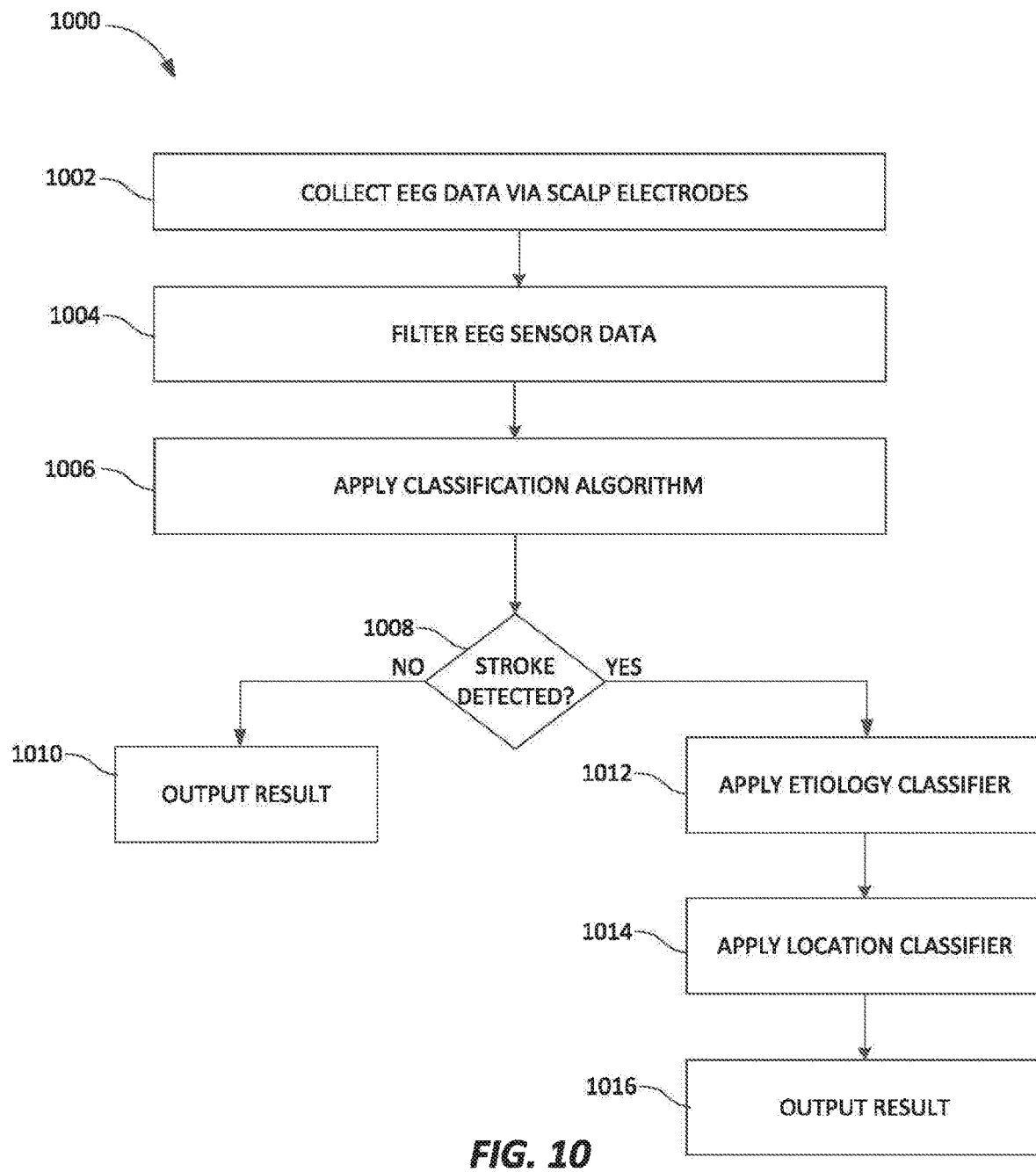
FIG. 10 is a flow diagram of another method for making a stroke determination in accordance with embodiments of the present technology.

FIG. 10 illustrates an example method 1000 for enhanced stroke detection. As illustrated, the process 1000 begins in block 1002 with collecting EEG sensor data via electrodes disposed at or adjacent the back of the neck or base of the skull (e.g., the target region 401 shown in FIG. 4). In some embodiments, the EEG sensor data can include electrical signals detected using electrodes of a sensor device 110, 210, or 310 as described above with respect to FIGS. 1-3. Such a device can be disposed (e.g., either implanted subcutaneously or positioned over the patient's skin) at the target region 401 (FIG. 4).

The process 1000 continues in block 1004 with filtering the EEG sensor data to remove ECG artifacts as described elsewhere herein. In block 1006, a classification algorithm is applied. The classification algorithm can be, for example, an algorithm adapted from the use of artificial intelligence (e.g., machine learning, neural networks, etc.) as applied to patient stroke data, for example as described above with respect to FIGS. 6 and 7. Based on the classification algorithm, in block stroke determination is made, which may be binary or probabilistic. In block 1008, if a stroke is detected (e.g., a probabilistic determination falls below some pre-determined threshold, for example less than 15% probability of a patient stroke based on the classifier algorithm), the result can be output in block 1010. If a stroke is detected in block 1008 (e.g., a probabilistic determination exceeds some pre-determined threshold, for example 85% likelihood of stroke), then the process 1000 continues to block 1012 to apply an etiology classifier. In some embodiments, such an etiology classifier can make a determination (probabilistic or definitive) of the origin of the stroke (e.g., ischemic or hemorrhagic). Such determinations can be made based on collected EEG sensor data alone or in conjunction with additional physiological parameters or patient data. In block 1014, a location classifier is applied. This classifier can determine a location of the stroke. For example, the location determination can include a left-versus-right hemisphere determination (e.g., a binary output or probabilistic result). In some embodiments, the location determination can include a more precise mapping of brain regions with particular probabilities assigned, for example a 70% probability of the stroke location being at a particular point on the patient's brain. The stroke location may be output along a spherical surface map or other suitable coordinate system for identifying the location in the patient's brain. In block 1016, the result of the classifiers can be output, for example via graphical display, automatic alert to call center, patient, or other entity, etc. In some embodiments, the output can include a graphical representation of the stroke location, for example as a superimposed location over a graphical representation of a brain.

In addition to outputting the results, information or instructions can also be output to a patient or user. The information or instructions can be output via a display device (e.g., the display 151 of FIG. 1). For example, if a stroke is identified in block 1008, then the system may provide instructions to route the patient to a comprehensive stroke treatment center or otherwise flag the patient for treatment. In embodiments in which the process 1000 is performed while the patient is in an ambulance, the process 1000 can output information or instructions to an emergency medical technician (EMT) or other personnel in the rear of the ambulance and/or to the ambulance driver. In some embodiments, the display to the ambulance driver can include navigational information such as a map and instructions to take the patient to a particular hospital or facility with a stroke center.

Figure 11:
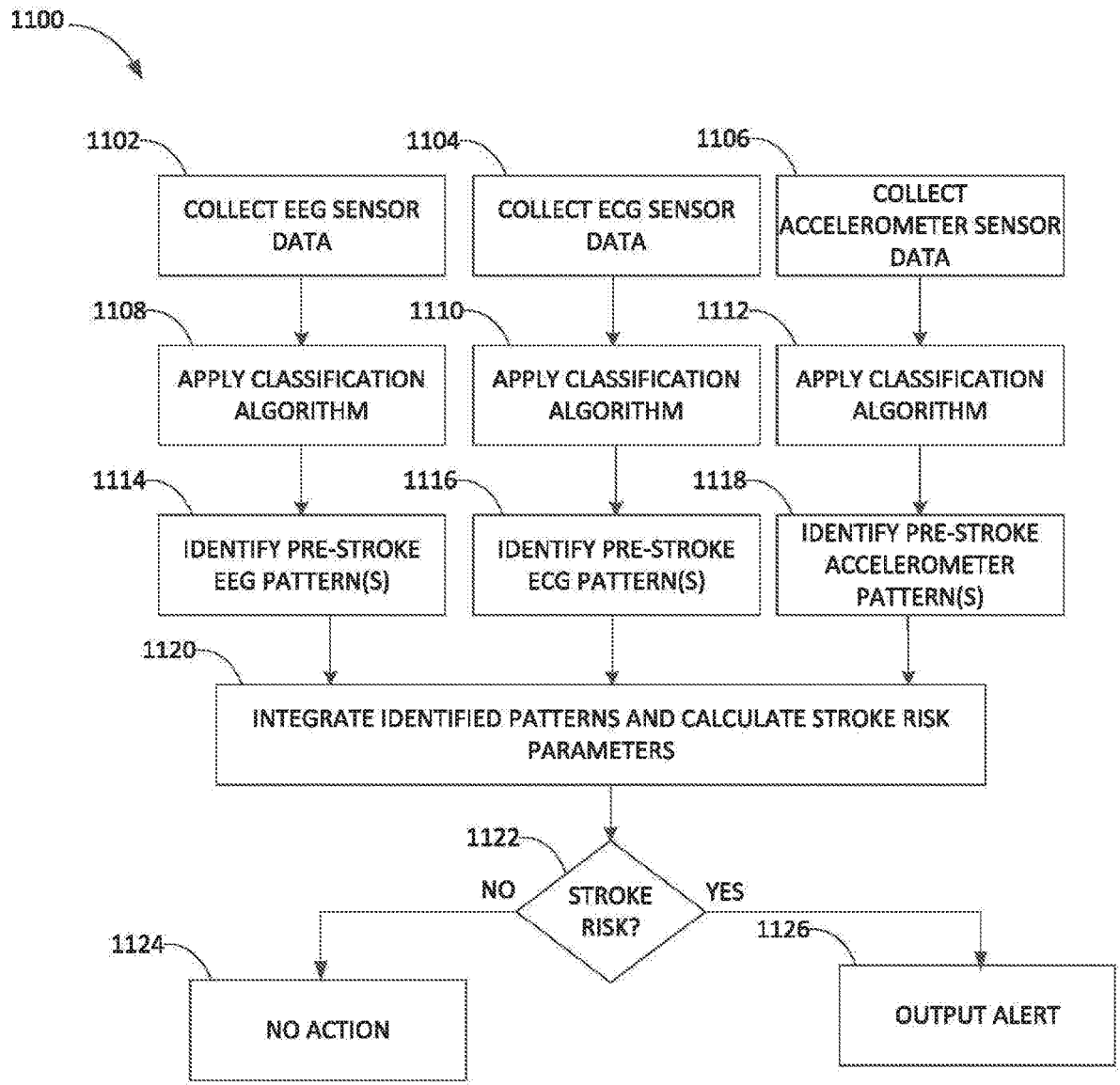
FIG. 11 is a flow diagram of another method for making a stroke determination in accordance with embodiments of the present technology.

FIG. 11 illustrates an example method 1100 for detecting a stroke and/or determining a patient's risk of stroke. In block 1102, 1104, and 1106, the method 1100 includes collecting EEG sensor data, ECG sensor data, and accelerometer sensor data, respectively. In some embodiments, fewer data can be collected, and in other embodiments additional data can also be collected (e.g., body temperature, blood pressure, etc.). In blocks 1108, 1110, and 1112, classification algorithms are applied to the respective data collected, and based on the classification algorithms, pre-stroke patterns are identified in blocks 1114, 1116, and 1118. In some embodiments, the classification algorithms can be generated from adaptive neural network models or other machine learning techniques trained on large samples of patient stroke data to identify particular patterns that are indicative of pre-stroke states. Such data may be more readily collected by the use of implantable monitoring devices as described herein.

In block 1120, the identified patterns can be integrated or otherwise combined and a stroke risk parameter can be calculated. The stroke risk can be based on the physiological data as well as other patient parameters (e.g., gender, age, history of stroke or heart conditions, etc.), and can include a probabilistic output of a patient's risk for stroke over. If, in block 1122, there is no risk of stroke identified (e.g., the stroke risk parameter falls below a pre-defined threshold), then no action is taken in block 11124. Optionally, a result of "no risk" or "low risk" can be output to the patient or other entity. If, in block 1122, a stroke risk is identified (e.g., the stroke risk parameter exceeds a pre-determined threshold) then an alert can be output in block 1126. Such an alert can be provided to the patient (e.g., via the external device 150), to a call center, a patient's medical team, or any other suitable entity.

Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Unless otherwise indicated, all numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising," and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments. For example, a master-slave configuration could be possible leveraging the well-established pectoral implant location to derive cardiac ECG information and the back-of-head/neck implant location to derive neuro EEG information. These slave devices can be converged into a master device that could be an external smartwatch or smartphone to provide stroke detection capability.

The invention claimed is:

1. A stroke detection system comprising:
   a sensor device configured to obtain physiological data from a patient, wherein the sensor device comprises a housing and a plurality of electrodes disposed on the housing and the housing is configured to be disposed at a portion of a neck or a head of the patient, and the physiological data comprises electrical brain activity data and electrical heart activity data of the patient sensed via the plurality of electrodes; and
   processing circuitry configured to:
   determine that instructions were output to the patient that instruct the patient to perform one or more actions;
   receive, from the sensor device, at least a portion of the physiological data during an attempt by the patient to perform the one or more actions;
   analyze at least the portion of the physiological data during the attempt by the patient to perform the one or more actions to generate a patient stroke indicator; and
   based on the analysis, generate the patient stroke indicator,
   wherein the patient stroke indicator includes at least one of:
   determining whether a patient has suffered a stroke,
   determining a risk that a patient will suffer a stroke,
   determining a location of a stroke,
   providing a confidence score associated with a determination of patient stroke, or
   classifying an identified stroke as ischemic or hemorrhagic.

2. The system of claim 1, wherein the sensor device is configured to detect brain activity data corresponding to activity in at least one of the P3, Pz, and P4 brain regions via the plurality of electrodes.

3. The system of claim 1, wherein the sensor device is configured to be disposed at or adjacent a rear portion of a neck or skull base of the patient.

4. The system of claim 1, wherein the housing is configured to be implanted within the patient.

5. The system of claim 4, wherein the housing is configured to be implanted subcutaneously.

6. The system of claim 1, wherein the housing is configured to be disposed over skin of the patient.

7. The system of claim 1, wherein the processing circuity comprises processing circuitry of the sensor device.

8. The system of claim 1, further comprising a computing device configured to be communicatively coupled to the sensor device and receive the physiological data from the sensor device, wherein the processing circuitry comprises processing circuitry of the computing device.

9. The system of claim 1, wherein the processing circuitry is configured to analyze the physiological data by at least filtering the physiological data to separate the electrical brain activity data from the electrical heart activity data.

10. The system of claim 9, wherein the processing circuitry is configured to analyze both the electrical brain activity data and the electrical heart activity data and generate the patient stroke indicator based on the analysis of both the electrical brain activity data and the electrical heart activity data.

11. The system of claim 10, wherein the processing circuitry is configured to apply a respective classification algorithm to each of the electrical brain activity data and the electrical heart activity data, and generate the patient stroke indicator based on classifications by the algorithms.

12. The system of claim 1, wherein the physiological data comprises motion data, and wherein the processing circuitry is further configured to analyze the motion data and generate the patient stroke indicator based on the analysis of the motion data.

13. The system of claim 12, wherein the processing circuitry is configured to apply a respective classification algorithm to each of the electrical brain activity data, the electrical heart activity data, and the motion data, and generate the patient stroke indicator based on classifications by the algorithms.

14. The system of claim 12, wherein the processing circuity is configured to make a fall determination based on the analysis of the motion data.

15. The system of claim 1, further comprising further comprising a computing device configured to:
communicate with the sensor device; and
instruct the patient to perform the one or more actions.

16. The system of claim 15, wherein the physiological data comprises first physiological data, and the computing device comprises one or more sensors configured to obtain second physiological data during the attempt to perform the one or more actions by the patient.

17. The system of claim 16, wherein the one or more sensors of the computing device comprise one or more of a camera or a microphone.

18. The system of claim 1, wherein the patient stroke indicator is probabilistic.

19. The system of claim 18, wherein the processing circuitry is further configured to generate a probabilistic etiology classification of a stroke.

20. A device comprising:
at least one housing configured to be disposed at a rear portion of a neck or skull base of a patient; and
a plurality of electrodes disposed on the housing, the electrodes configured to detect electrical signals corresponding to brain activity in at least the P3, Pz, and P4 brain regions of the patient;
processing circuitry configured to:
determine that instructions were output to the patient that instruct the patient to perform one or more actions;
receive at least a portion of the detected electrical signals during an attempt by the patient to perform the one or more actions;
analyze at least the portion of the electrical signals during the attempt by the patient to perform the one or more actions to generate a patient stroke indicator; and
generate the patient stroke indicator based on the analysis,
wherein the patient stroke indicator includes at least one of:
determining whether a patient has suffered a stroke,
determining a risk that a patient will suffer a stroke,
determining a location of a stroke,
providing a confidence score associated with a determination of patient stroke, or
classifying an identified stroke as ischemic or hemorrhagic.

21. The device of claim 20, wherein the device is configured to be implanted within the patient.

22. The device of claim 20, wherein the device is configured to be disposed over skin of the patient.

23. The device of claim 20, wherein the at least one housing has a volume of less than about 1.2 cc.

24. A method for detecting strokes, the method comprising:
obtaining physiological data from a patient via a plurality of electrodes disposed on a housing of a sensor device disposed at a rear portion of a neck or base of a skull of the patient;
determining that instructions were output to the patient that instruct the patient to perform one or more actions;
receiving, from the sensor device, at least a portion of the physiological data during an attempt by the patient to perform the one or more actions;
analyzing at least the portion of the physiological data obtained during the attempt by the patient to perform the one or more actions to generate a patient stroke indicator; and
based on the analysis, generating the patient stroke indicator,
wherein the patient stroke indicator includes at least one of:
determining whether a patient has suffered a stroke,
determining a risk that a patient will suffer a stroke,
determining a location of a stroke,
providing a confidence score associated with a determination of patient stroke, or
classifying an identified stroke as ischemic or hemorrhagic.

25. The method of claim 24, wherein obtaining physiological data comprises detecting electrical brain activity via the plurality of electrodes of the sensor device, the electrical brain activity corresponding to activity in at least one of the P3, Pz, and P4 brain regions of the patient.

26. The method of claim 24, wherein the physiological data comprises electrical brain activity data and electrical heart activity data, and wherein analyzing the physiological data comprises filtering the physiological data to separate the electrical brain activity data from the electrical heart activity data.

27. The method of claim 24, wherein the physiological data comprises electrical brain activity data and electrical heart activity data, and wherein analyzing the physiological data comprises:
analyzing both the electrical brain activity data and the electrical heart activity data; and
generating the patient stroke indicator based on the analysis of both the electrical brain activity data and the electrical heart activity data.

28. The method of claim 27, wherein analyzing the physiological data comprises applying a respective classification algorithm to each of the electrical brain activity data and the electrical heart activity data, and wherein generating the patient stroke indicator comprises generating the patient stroke indicator based on classifications by the algorithms.

29. The method of claim 24, wherein the physiological data comprises motion data.

30. The method of claim 29, wherein the physiological data further comprises electrical brain activity data and electrical heart activity data, and
wherein analyzing the physiological data comprises applying a respective classification algorithm to each of the electrical brain activity data, the electrical heart activity data, and the motion data, and wherein generating the patient stroke indicator comprises generating the patient stroke indicator based on classifications by the algorithms.

31. The method of claim 29, wherein analyzing the physiological data comprises making a fall determination based on the motion data.

32. The method of claim 24, wherein the sensor device is implanted subcutaneously within the patient.

33. The method of claim 24, wherein the sensor device is disposed over skin of the patient.

34. The method of claim 24, wherein the patient stroke indicator is probabilistic.

35. The method of claim 34, further comprising generating a probabilistic etiology classification of a stroke.

* * * * *